(12) United States Patent
Nohmi et al.

(10) Patent No.: US 11,391,940 B2
(45) Date of Patent: Jul. 19, 2022

(54) INDUSTRIAL ENDOSCOPE, OBSERVATION METHOD, OBSERVATION DEVICE, UNDERWATER MACHINE, PUMP INSPECTION SYSTEM, UNDERWATER ROBOT CONTROL SYSTEM, AND UNDERWATER ROBOT CONTROL METHOD

(71) Applicant: EBARA CORPORATION, Tokyo (JP)

(72) Inventors: Motohiko Nohmi, Tokyo (JP); Yumiko Sekino, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 299 days.

(21) Appl. No.: 16/499,198

(22) PCT Filed: Jan. 22, 2018

(86) PCT No.: PCT/JP2018/001706
§ 371 (c)(1),
(2) Date: Sep. 27, 2019

(87) PCT Pub. No.: WO2018/179705
PCT Pub. Date: Oct. 4, 2018

(65) Prior Publication Data
US 2021/0109339 A1    Apr. 15, 2021

(30) Foreign Application Priority Data

Mar. 31, 2017 (JP) .............................. JP2017-070845
Apr. 3, 2017 (JP) .............................. JP2017-073644
(Continued)

(51) Int. Cl.
*G02B 23/24* (2006.01)
*B63C 11/52* (2006.01)
(Continued)

(52) U.S. Cl.
CPC ........ *G02B 23/2476* (2013.01); *B25J 9/1697* (2013.01); *B63C 11/52* (2013.01); *G02B 23/14* (2013.01)

(58) Field of Classification Search
CPC ........................... G02B 23/2476; B63C 11/52
(Continued)

(56) References Cited

U.S. PATENT DOCUMENTS 5,168,473 A   12/1992   Parra
5,579,285 A   11/1996   Hubert
(Continued)

FOREIGN PATENT DOCUMENTS

JP   S62-094500 A   4/1987
JP   H05-043115 U   6/1993
(Continued)

OTHER PUBLICATIONS

International Patent Application No. PCT/JP2018/001706; Int'l Search Report; dated Apr. 10, 2018; 16 pages.

*Primary Examiner* — Jeffery A Williams
(74) *Attorney, Agent, or Firm* — BakerHostetler

(57) ABSTRACT

Provided are various devices, systems and methods for observing pumps and the like.

Provided is an industrial endoscope including an imaging device, a flexible holding member configured to hold the imaging device, and one or a plurality of nozzles fixed to the holding member and which injects a fluid.

5 Claims, 26 Drawing Sheets

(30) Foreign Application Priority Data

Jun. 7, 2017 (JP) .............................. JP2017-112460
Jun. 9, 2017 (JP) .............................. JP2017-113959

(51) Int. Cl.
*B25J 9/16* (2006.01)
*G02B 23/14* (2006.01)

(58) Field of Classification Search
USPC .......................................................... 348/61
See application file for complete search history.

(56) References Cited

U.S. PATENT DOCUMENTS

| | | | |
|---|---|---|---|
| 2005/0004431 A1* | 1/2005 | Kogasaka | A61B 17/0469 600/117 |
| 2006/0139579 A1* | 6/2006 | Kasahara | G09B 27/00 353/94 |
| 2008/0117316 A1 | 5/2008 | Orimoto | |
| 2011/0063951 A1 | 3/2011 | Jiang et al. | |
| 2014/0313191 A1 | 10/2014 | Bruls et al. | |
| 2015/0168263 A1* | 6/2015 | Mueller | F01D 21/003 348/82 |
| 2016/0259029 A1 | 9/2016 | Jukkala | |
| 2017/0035268 A1* | 2/2017 | Kumar | G06T 15/80 |
| 2017/0059706 A1 | 3/2017 | Burlet et al. | |

FOREIGN PATENT DOCUMENTS

| | | | |
|---|---|---|---|
| JP | H07-095953 A | | 4/1995 |
| JP | H07-198844 A | | 8/1995 |
| JP | H08-061952 A | | 3/1996 |
| JP | H08-504944 A | | 5/1996 |
| JP | H08-248114 A | | 9/1996 |
| JP | H09-145821 A | | 6/1997 |
| JP | H10-111352 A | | 4/1998 |
| JP | H10-227847 A | | 8/1998 |
| JP | 2005-058904 A | | 3/2005 |
| JP | 2005-246578 A | | 9/2005 |
| JP | 2005-263092 A | | 9/2005 |
| JP | 2006-078329 A | | 3/2006 |
| JP | 2006-275827 A | | 10/2006 |
| JP | 2008-129439 A | | 6/2008 |
| JP | 2008-202575 A | | 9/2008 |
| JP | 2009-017241 A | | 1/2009 |
| JP | 2009-041503 A | | 2/2009 |
| JP | 2009041503 A | * | 2/2009 |
| JP | 2010-038873 A | | 2/2010 |
| JP | 2011-059108 A | | 3/2011 |
| JP | 2011-226873 A | | 11/2011 |
| JP | 2014-170015 A | | 9/2014 |
| JP | 2014-528794 A | | 10/2014 |
| JP | 2014-233005 A | | 12/2014 |
| JP | 2015-503258 A | | 1/2015 |
| JP | 2015-066538 A | | 4/2015 |
| JP | 2015-096707 A | | 5/2015 |
| JP | 2015-230625 A | | 12/2015 |
| JP | 2017-058308 A | | 3/2017 |
| JP | 2017-508162 A | | 3/2017 |
| WO | WO 2017/010060 A1 | | 1/2017 |

* cited by examiner

INDUSTRIAL ENDOSCOPE, OBSERVATION METHOD, OBSERVATION DEVICE, UNDERWATER MACHINE, PUMP INSPECTION SYSTEM, UNDERWATER ROBOT CONTROL SYSTEM, AND UNDERWATER ROBOT CONTROL METHOD

TECHNICAL FIELD

The present disclosure relates to an industrial endoscope, an observation method, an observation device, an underwater machine, a pump inspection system, an underwater robot control system, and an underwater robot control method.

BACKGROUND ART

Various devices and techniques for observing pumps and the like have been proposed.

CITATION LIST

Patent Literature

Patent Literature 1: JP 2008-202575 A
Patent Literature 2: JP 2015-96707 A
Patent Literature 3: JP 2005-246578 A

SUMMARY OF INVENTION

Technical Problem

Various devices, systems, and methods for observing pumps and the like are provided.

Solution to Problem

There is provided an industrial endoscope including an imaging device, a flexible holding member configured to hold the imaging device, and one or a plurality of nozzles fixed to the holding member and which injects a fluid.

DESCRIPTION OF EMBODIMENTS (First Aspect)

TECHNICAL FIELD

A first aspect relates to an industrial endoscope and an observation method.

BACKGROUND ART

A general industrial endoscope is provided with an imaging device at a distal end, and a vicinity of the distal end is bent to change the position of the imaging device.

[Outline of First Aspect]
[Problem to be Solved by First Aspect]

However, there is a problem that a movable range of the imaging device is narrow only by bending of the distal end, and an observable range by the industrial endoscope is limited.

The first aspect has been made in view of such a problem, and an objective of the first aspect is to provide an industrial endoscope and an observation method for largely moving an imaging device.

Solution to Problem

There is provided an industrial endoscope including an imaging device, a flexible holding member configured to hold the imaging device, and one or a plurality of nozzles fixed to the holding member and which injects a fluid.

With injection of the fluid, the imaging device can be largely moved. As a result, an observable range can expand. Further, in a case where branches are included in a capture target, the imaging device can be caused to proceed to a desired branch.

It is desirable that the imaging device held by the holding member moves in a direction different from an injecting direction of the fluid through the nozzle as the nozzle injects the fluid.

The plurality of nozzles may include a first nozzle that injects the fluid in a capturing direction of the imaging device, and a second nozzle that injects the fluid in an opposite direction to the capturing direction of the imaging device.

With the configuration, the imaging device can be advanced or retracted.

The industrial endoscope may further include a coating member that covers the imaging device, the holding member, and the one or the plurality of nozzles.

With the configuration, the risk of being caught in the observation target can be reduced, and infiltration of water into an interior of the industrial endoscope is less likely to occur even in a case of an observation in water.

It is desirable that one flow path through which the fluid flows is provided, and the plurality of nozzles includes two or more nozzles connected to the one flow path, and valves for controlling whether injecting the fluid are respectively provided to the two or more nozzles.

With the configuration, the numbers of flow paths and supply sources of fluid can be reduced.

There is provided an observation method of performing an observation while moving an imaging device held by a holding member by injecting a fluid through a nozzle fixed to the holding member.

With injection of the fluid, the imaging device can be largely moved. As a result, an observable range can expand.

[Effect of First Aspect]

The imaging device can be largely moved.

[Mode for Implementing First Aspect]

Hereinafter, an embodiment according to the first aspect will be specifically described with reference to the drawings.

Figure 1:
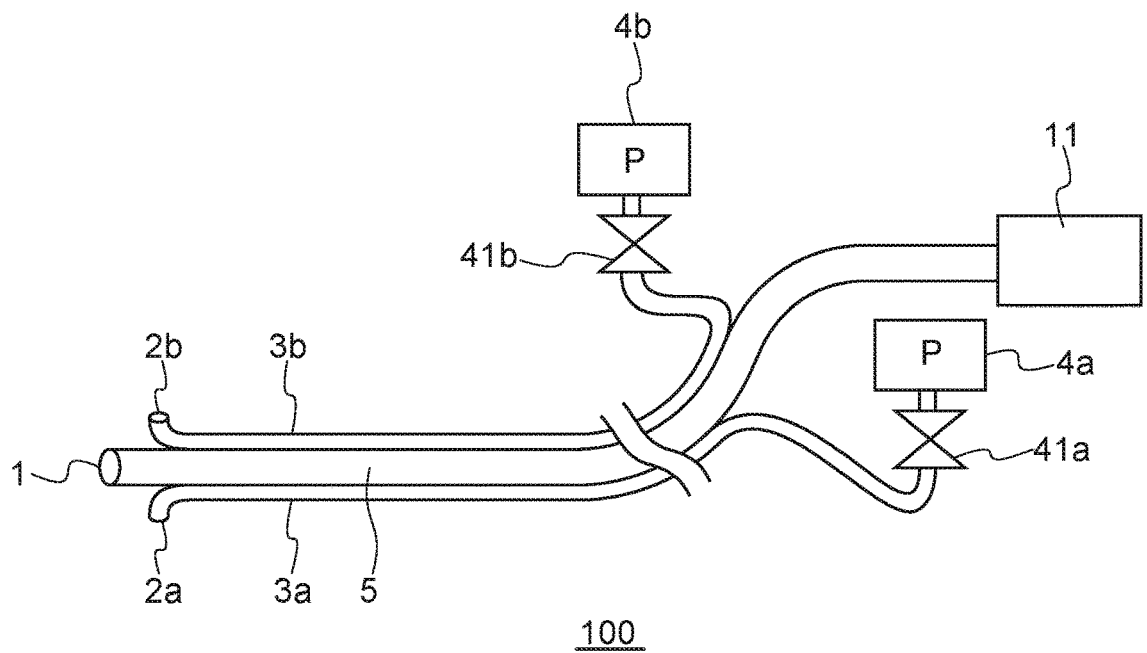
FIG. 1 is a schematic configuration view of an industrial endoscope 100 according to an embodiment.

FIG. 1 is a schematic configuration view of an industrial endoscope 100 according to an embodiment. The industrial endoscope 100 includes an imaging device 1, nozzles 2a and 2b, flow paths 3a and 3b, high pressure sources 4a and 4b, and a holding member 5, and is used for observation of an interior of a pump, for example.

The imaging device 1 may be a camera provided with a lens at a distal end or may be optical fiber. The imaging device 1 is held at a distal end of the flexible holding member 5. Wiring connected to the imaging device 1 passes through the holding member 5, and power supply and control of the imaging device 1 are performed from the outside, and image data obtained in the imaging device 1 is transmitted to an image processing system 11. An imaged image is displayed in real time on a monitor (not illustrated) arranged near an operator, and capture or recording is also possible as appropriate.

The nozzle 2a is attached to an end of the flexible flow path 3a. The high pressure source 4a is connected to the other end of the flow path 3a via a valve 41a. The flow path 3a is directly or indirectly fixed to the holding member 5. Therefore, it can be said that the nozzle 2a is fixed to the holding member 5 or the imaging device 1. The high pressure source 4a may be a tank or a pump that supplies a liquid such as water, or may be a compressor that supplies a gas such as air. That is, any high pressure source 4a is adoptable as long as the high pressure source 4a supplies a fluid via the flow path 3a. By providing the flow path 3a and the high pressure source 4a, the nozzle 2a can inject the fluid through its tip end.

The nozzle 2b, the flow path 3b, and the high pressure source 4b have a similar configuration. Note that a fluid injecting direction through the nozzle 2a and a fluid injecting direction through the nozzle 2b are different from each other, and are opposite directions by 180 degrees in the specific example in FIG. 1.

Figure 2:
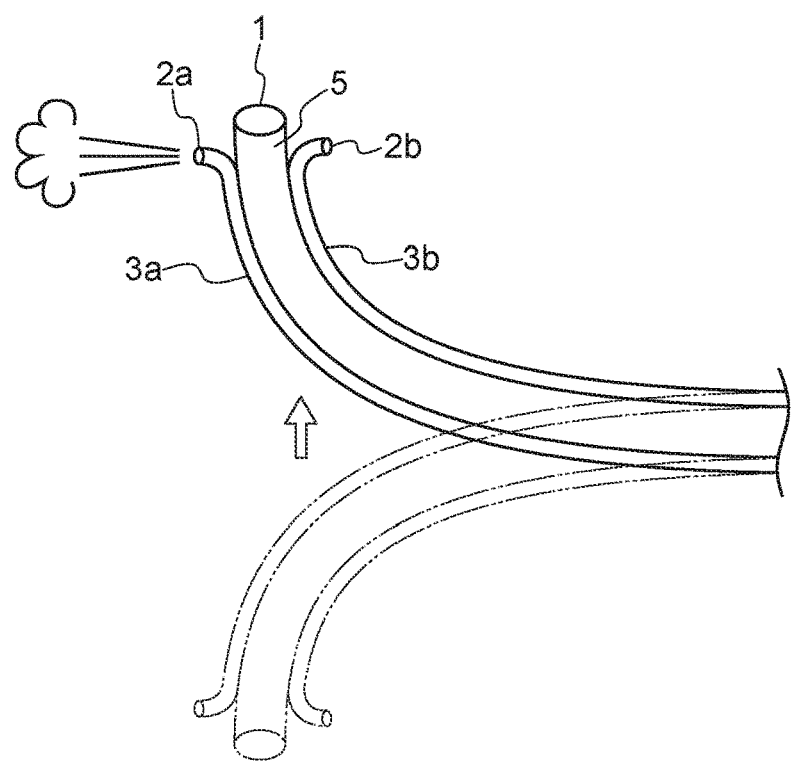
FIG. 2 is a view for describing an operation of the industrial endoscope 100.

FIG. 2 is a view for describing an operation of the industrial endoscope 100. As illustrated in FIG. 2, in a case where the fluid is injected only through the nozzle 2a, the holding member 5 that holds the imaging device 1 and the flow paths 3a and 3b largely change the direction from the fluid injecting direction (to be specific, to an opposite direction), and as a result, the imaging device 1 is moved and an imaging position is changed. Although not illustrated, when the fluid is injected only through the nozzle 2b, the imaging device 1 is again moved to a direction different from the injecting direction. In this manner, any observation target can be observed while moving the imaging device 1. In particular, in a case where branches are included in the observation target, the imaging device 1 can be caused to proceed to a desired branch.

Figure 3:
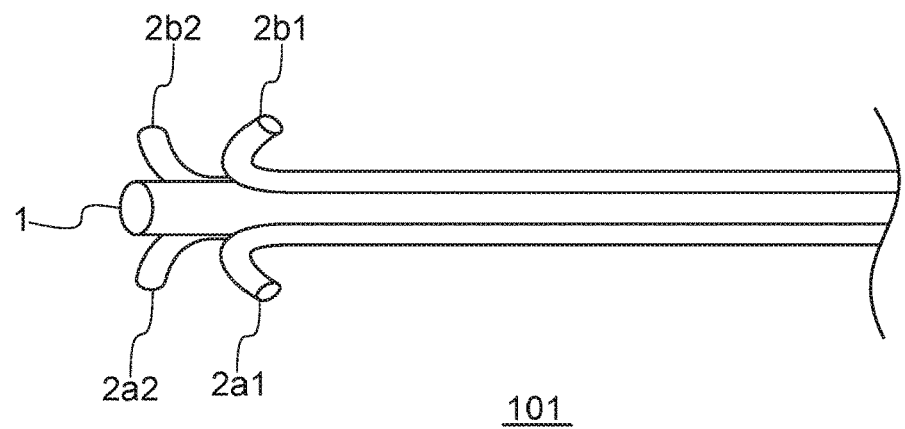
FIG. 3 is a schematic configuration view of an industrial endoscope 101 as a first modification.

FIG. 3 is a schematic configuration view of an industrial endoscope 101 as a first modification. As illustrated in FIG. 3, a larger number of nozzles 2a1, 2a2, 2b1, and 2b2 may be provided to increase the degree of freedom of moving the imaging device 1.

Figure 4:
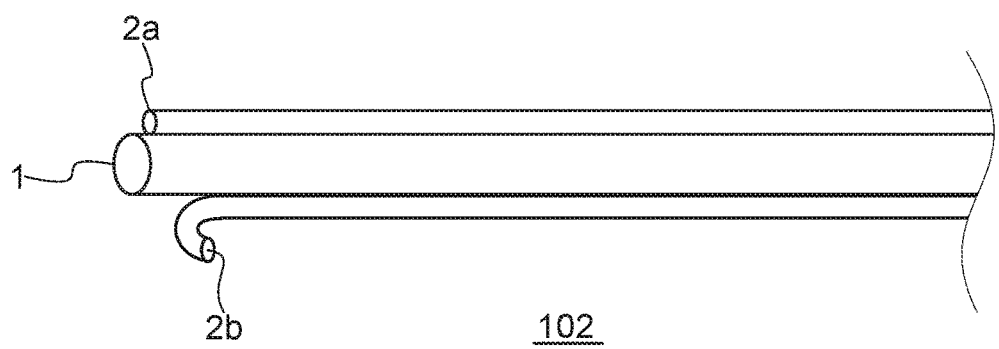
FIG. 4 is a schematic configuration view of an industrial endoscope 102 as a second modification.

FIG. 4 is a schematic configuration view of an industrial endoscope 102 as a second modification. As illustrated in FIG. 4, a nozzle 2a that injects a fluid in a capturing direction (forward) of an imaging device 1 and a nozzle 2b that injects a fluid in an opposite direction (backward) to the capturing direction may be provided. By injecting the fluid only through the nozzle 2a, the industrial endoscope 102 moves backward. By injecting the fluid only through the nozzle 2b, the industrial endoscope 102 moves forward.

Figure 5:
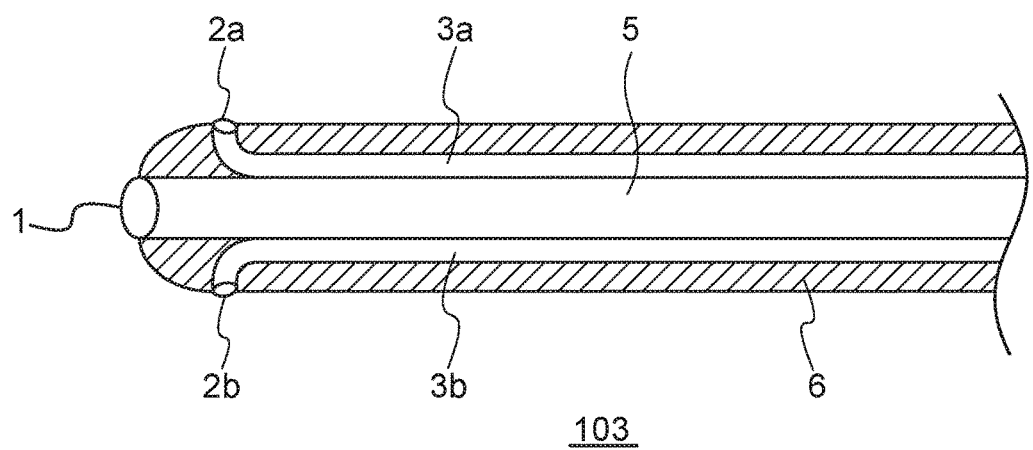
FIG. 5 is a schematic configuration view of an industrial endoscope 103 as a third modification.

FIG. 5 is a schematic configuration view of an industrial endoscope 103 as a third modification. As illustrated in FIG. 5, this industrial endoscope 103 includes a coating member 6 that covers flow paths 3a and 3b to which nozzles 2a and 2b are respectively attached and a holding member 5. When an observation in water is performed for a pump or the like, the coating member 6 serves as a protective material and suppresses infiltration of water into the industrial endoscope 103. Further, by forming the coating member 6 into a tubular shape, the vicinity of the nozzle 2a becomes smooth and a surface of the industrial endoscope 103 has less unevenness and is less likely to be caught in the observation target.

Figure 6:
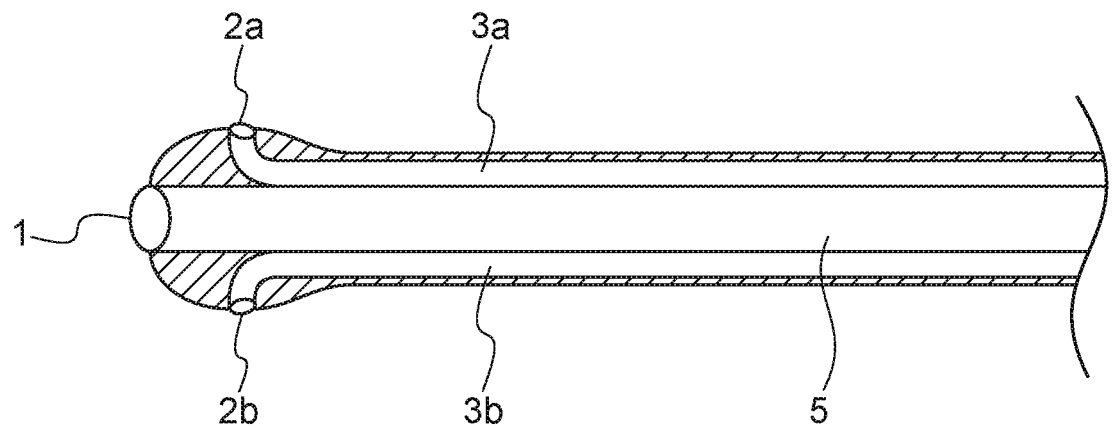
FIG. 6 is a schematic configuration view of an industrial endoscope 104 according to a fourth modification.

FIG. 6 is a schematic configuration view of an industrial endoscope 104 according to a fourth modification.

As illustrated in FIG. 6, a coating member 6 in the vicinity of nozzles 2a and 2b may be thickened.

Figure 7:
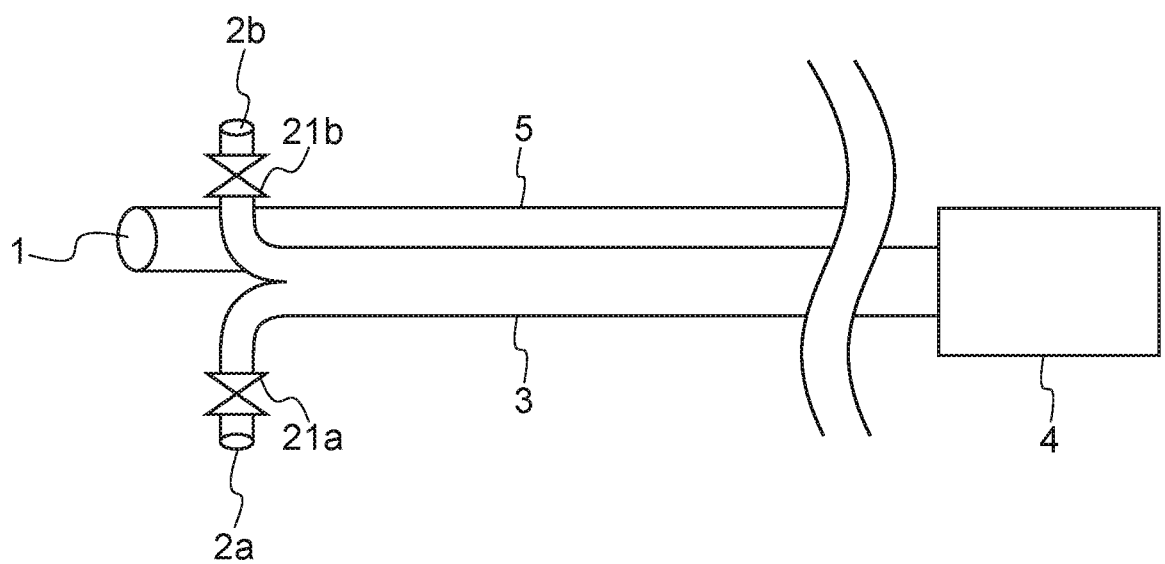
FIG. 7 is a schematic configuration view of an industrial endoscope 105 according to a fifth modification.

FIG. 7 is a schematic configuration view of an industrial endoscope 105 according to a fifth modification. As illustrated in FIG. 7, one flow path 3 having one end connected with one high pressure source 4 may be branched, and two or more nozzles 2a and 2b may be connected to the branched ends. In this case, the nozzles 2a and 2b are provided with valves 21a and 21b, respectively. It is desirable to remotely control the valves 21a and 21b using electric wires, radio waves, sonic waves, light, wires, or the like.

By opening the valve 21a and closing the valve 21b, a fluid is injected only through the nozzle 2a. On the other hand, by opening the valve 21b and closing the valve 21a, a fluid is injected only through the nozzle 2b. With such a configuration, the numbers of the flow paths 3 and the high pressure sources 4 can be reduced.

The above-described two or more modifications may be arbitrarily combined.

As described above, in the present embodiment, the fluid is injected through the nozzles, the imaging device 1 can be largely moved and the observable range expands.

REFERENCE SIGNS LIST

1 Imaging device
11 Image processing system
2a, 2a1, 2a2, 2b, 2b1, 2b2 Nozzle
3, 3a, 3b Flow path
4, 4a, 4b High pressure source
5 Holding member
6 Coating member
11 Image processing system (Second Aspect)

Technical Field

A second aspect relates to an observation device for observing an interior of a pump and a pump observation method.

Background Art

Underwater machines such as pumps are deteriorated, and wear and corrode as they continue to be used, and thus periodical observation is required.

[Outline of Second Aspect]
[Problem to be Solved by Second Aspect]

Water such as muddy water with low transparency, chemicals, or colored organisms are often present around underwater machines, and conducting an observation is not easy.

The second aspect has been made in view of such a problem, and an objective of the second aspect is to provide an observation device and an observation method for enabling an observation of an underwater machine, and to provide an underwater machine that is easy to observe.

Solution to Problem

There is provided an observation device including an imaging device, an injection port through which a liquid is injected toward an imaging direction by the imaging device, and a water purification member provided on a flow path from a supply source of the liquid to the injection port.

The liquid in the supply source of the liquid may be muddy water, and the muddy water may become a clean liquid by being filtered by the water purification member and injected through the injection port.

Alternatively, the liquid in the supply source of the liquid may be a chemical liquid, and the chemical liquid may become a clean liquid by being neutralized by the water purification member and injected through the injection port.

There is provided an observation method including purifying a liquid by a water purification member, injecting the purified liquid into a place between an imaging device and an observation target, and capturing, by the imaging device, the observation target in a state where the purified liquid exists between the imaging device and the observation target.

There is provided an observation device including an imaging device, a first injection port through which a fluid is injected toward an imaging direction by the imaging device, and a thrust balancer configured to generate thrust in an opposite direction to thrust by the fluid injection through the first injection port.

The thrust balancer may include a second injection port through which a fluid is injected in an opposite direction to an injecting direction of the fluid through the first injection port.

Alternatively, the thrust balancer may be a screw.

There is provided an observation method including injecting a fluid to an observation target existing in a second direction opposite to a first direction while generating thrust in the first direction, and capturing, by an imaging device, the observation target in a state where the fluid exists between the imaging device and the observation target.

There is provided an observation method including injecting a fluid having a higher degree of transparency than an opaque liquid to a recess in an observation target placed in the opaque liquid, and observing, by an imaging device, an inner surface of the recess in a state where the fluid is stored in the recess.

There is provided an underwater machine including an injection port through which a fluid is injected provided near an observation target place.

There is provided an observation method including injecting a fluid having a higher degree of transparency than an opaque liquid through an injection port provided near an observation target place placed in the opaque liquid, and observing, by an imaging device, the observation target place in a state where the fluid exists between the observation target place and the imaging device.

[Mode for Implementing Second Aspect]

Hereinafter, an embodiment according to the second aspect will be specifically described with reference to the drawings. Note that reference numerals are assigned independently of the first aspect.

Figure 8:
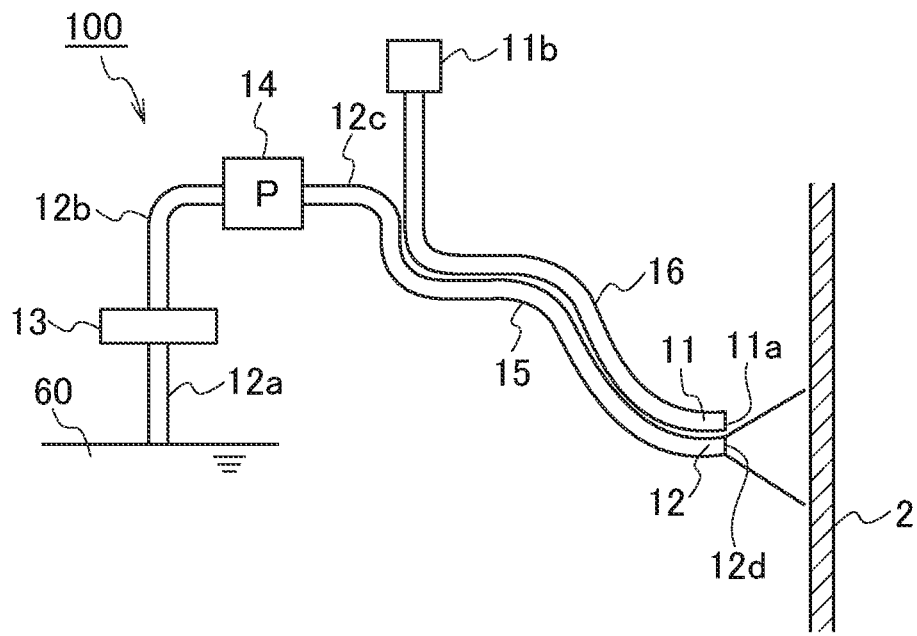
FIG. 8 is a schematic configuration view of an observation device 100 according to a first embodiment.

FIG. 8 is a schematic configuration view of an observation device 100 according to a first embodiment. The observation device 100 may be an industrial endoscope, an underwater robot, an underwater drone, or the like, and may include an imaging device 11, flow paths 12a to 12c, a filter 13 (water purification member), a pump 14, an injection member 15, and a holding member 16.

The imaging device 11 images the front of a lens 11a provided at a distal end of the imaging device 11. The imaging device 11 may be a fiber scope (not illustrated) having a lens 11a attached to a distal end, or a camera having a lens 11a. The imaging device 11 is held by the holding member 16. Wiring connected to the imaging device 11 passes through the holding member 16, and power supply and control of the imaging device are performed from the outside, and image data obtained in the imaging device 11 is transmitted to an image processing system 11b. An imaged image is displayed in real time on a monitor (not illustrated) arranged near an operator, and capture or recording is also possible as appropriate.

One end of the flow path 12a is connected to a liquid supply source 60 and the other end is connected to the filter 13. One end of the flow path 12b is connected to the filter 13 and the other end is connected to the pump 14. One end of the flow path 12c is connected to the pump 14 and the other end is connected to the injection member 15. In other words, the filter 13 and the pump 14 are sequentially provided on the flow paths 12a to 12c from the liquid supply source 60 to the injection member 15.

A liquid from the liquid supply source 60 is sucked up by the filter 13 by driving of the pump 14, passes through the pump 14, and is injected through an injection port 12d provided in a distal end of the injection member 15.

The liquid supply source 60 may be a separate water source (for example, a public water supply) such as a tank in which a clean liquid is stored in advance. However, hereinafter, assuming that the liquid supply source 60 is a suction water tank or a discharge water tank in a drainage plant, and the liquid in the liquid supply source 60 is an opaque liquid containing mud (so-called muddy water). The muddy water from the liquid supply source 60 becomes a clean liquid as passing through the filter 13, and flows into the pump 14. Then, this clean liquid is injected through the injection port 12d. Note that "clean" means that at least the filtered liquid has a higher degree of transparency than the liquid in the liquid supply source 60.

The liquid is injected through the injection port 12d toward an imaging direction by the imaging device 11. In other words, the injection port 12d causes the liquid to be injected into between the lens 11a of the imaging device 11 and an observation target.

The holding member 16 holds the imaging device 11 at its distal end, and has flexibility. At least a part of the holding member 16 may be coupled to at least a part of the flow paths 12a to 12c or may be integrated. An operation module (not illustrated) such as a joystick is provided at the root of the holding member 16 (an end opposite to an end where the lens 11a is provided). When an operator manipulates the operation module, the direction of the distal end of the holding member 16 (that is, the direction of the lens 11a) can be adjusted. Further, a control device (not illustrated) that controls injection of the liquid and imaging is also provided at the root of the holding member 16.

Note that the aspect illustrated in FIG. 8 is merely an example, and in a case where the observation device 100 is a large underwater robot or a large underwater drone, the filter 13 and the pump 14 may be provided in the underwater robot or the underwater drone itself, and the clean liquid may be generated from an ambient liquid.

An observation is performed using the observation device 100 as follows. First, the operator detects an observation target position in an observation target 2 by manipulating the operation module while observing a picture imaged by the imaging device 11 on the monitor. Note that muddy water may exist around the observation target 2.

When the observation target position is found, the clean liquid is injected through the injection port 12d toward the imaging direction by the imaging device 11, by an operation of the operator. More specifically, the muddy water from the liquid supply source 60 is brought to pass through the filter 13 and is filtered by driving of the pump 14 to generate the clean liquid. Then, this clean liquid is injected to between the lens 11a and the observation target position.

As a result, a water path by the injected clean liquid is formed between the front of the lens 11a and the observation target position. In this state, the operator observes the picture imaged by the imaging device 11 on the monitor, and captures the observation target when the water path is formed and the observation target position can be seen.

As described above, in the first embodiment, the clean liquid obtained by filtering muddy water is injected in front of the lens 11a. Therefore, even when dirty water is present between the lens 11a and the observation target position, an observation of the observation target position becomes easy.

Note that it is desirable to arrange the filter 13 upstream of the pump 14 to cause the clean liquid to flow into the pump 14. However, the filter 13 may be arranged downstream of the pump 14 as long as the pump 14 can drive the muddy water.

Further, in the case where the liquid from the liquid supply source 60 is a chemical liquid, a water purification member for performing neutralization or the like may be provided in place of or in addition to the filter 13. Furthermore, in the case where the observation target is a device under the sea, transparent sea water may be injected without through the filter 13. Further, a gas such as air may be injected instead of the liquid.

Second Embodiment

A second embodiment to be described next relates to stabilization of the observation device 100. In the first embodiment, when a liquid is injected through the injection port 12d, thrust is generated in the opposite direction (away from the observation target position). In particular, to push off dirty water, it is desirable to inject the liquid through the injection port 12d with as high pressure as possible, so that the thrust becomes larger.

In a case where the observation target is close to a bottom of water or a bottom of a liquid tank, the observation device 100 can be put on the bottom and can be made difficult to move due to friction between a lower surface of the observation device 100 and the bottom of water or the bottom of the liquid tank. However, if this is not the case, the observation device 100 cannot remain on the spot and moves, which may make the observation difficult. Although it is conceivable to make the observation device 100 sufficiently heavy, the observation device 100 is desirably small and light in view of workability.

Therefore, in the present embodiment, a following observation device 101 is provided.

Figure 9:
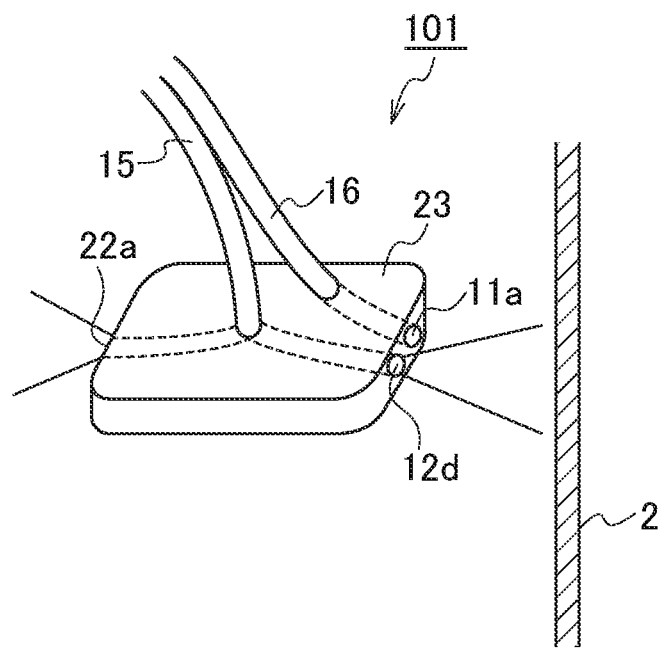
FIG. 9 is a schematic configuration view of an observation device 101 according to a second embodiment.

FIG. 9 is a schematic configuration view of the observation device 101 according to the second embodiment. Hereinafter, differences from the first embodiment will be mainly described. This observation device 101 has two injection ports 12d and 22a. The injection port 12d injects a liquid toward an imaging direction by an imaging device 11, similarly to the first embodiment. Meanwhile, the injection port 22a injects a liquid in an opposite direction to an injecting direction of the injection port 12d. As an example, the injection port 12d and a lens 11a of the imaging device 11 are provided in one surface of a base 23, and the injection port 22a is provided in an opposite surface.

Then, at the time of pump observation, the liquid is injected through the injection port 12d to an observation target position while generating thrust in a direction approaching an observation target 2 by liquid injection through the injection port 22a. As a result, thrust by the injection port 12d and the thrust by the injection port 22a are balanced, and the observation device 101 hardly moves and the observation of the observation target position becomes easy.

Note that, in the present embodiment, supply of the liquid to the injection ports 12d and 22a may be of the aspect described in the first embodiment, or may be from a tank or the like in which a clean liquid is stored in advance. Further, a liquid supply source to the injection ports 12d and 22a may be common or may be separately provided. Furthermore, in the present embodiment, a gas may be injected through the injection ports 12d and 22a, rather than a liquid.

Third Embodiment

A third embodiment to be described next is a modification of the second embodiment and is intended to balance thrust using a screw.

Figure 10:
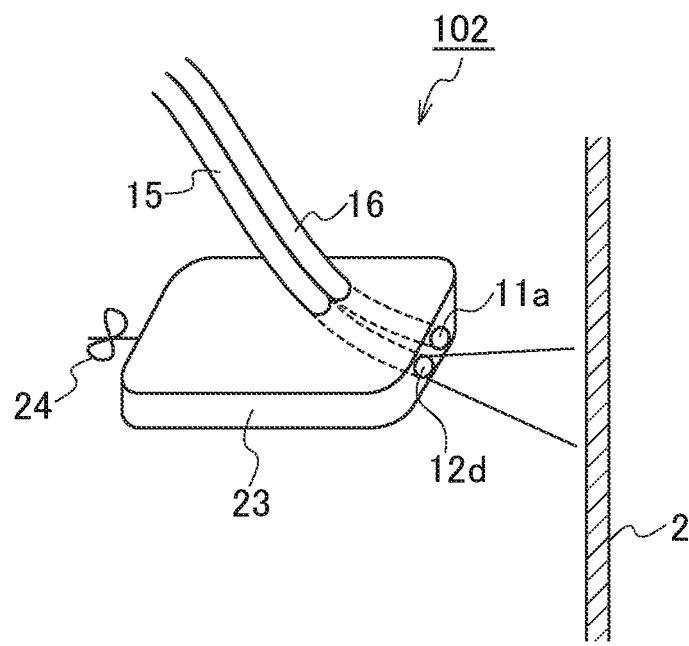
FIG. 10 is a schematic configuration view of an observation device 102 according to a third embodiment.

FIG. 10 is a schematic configuration view of an observation device 102 according to the third embodiment. Hereinafter, differences from the second embodiment will be mainly described. This observation device 102 includes a screw 24. As an example, an injection port 12d and a lens 11a of an imaging device 11 are provided in one surface of a base 23, and the screw 24 is provided on an opposite surface. Trust in a direction approaching an observation target is generated as the screw 24 is rotated.

In the present embodiment, at the time of pump observation, the liquid is injected through the injection port 12d to an observation target position while rotating the screw 24 to generate the thrust in a direction approaching an observation target. As a result, thrust by the injection port 12d and the thrust by the screw 24 are balanced, and the observation device 102 hardly moves and the observation of the observation target position becomes easy.

Fourth Embodiment

A fourth embodiment to be described next relates to an observation of a recess in an observation target.

Figure 11:
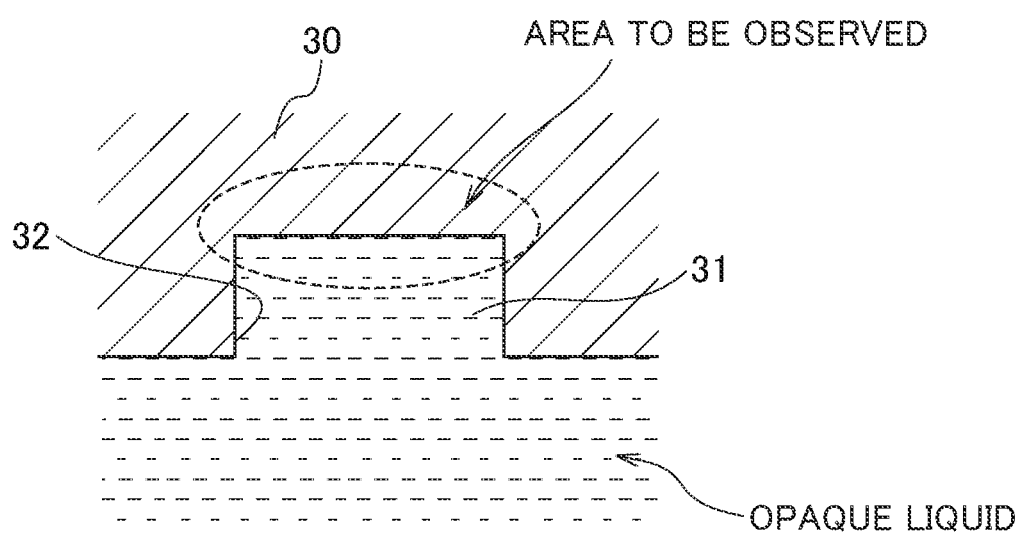
FIG. 11 is a view schematically illustrating an observation target 30 in a fourth embodiment.

FIG. 11 is a view schematically illustrating an observation target 30 in the fourth embodiment. As illustrated in FIG. 11, the observation target 30 of the present embodiment is an arbitrary underwater machine (for example, a pump) placed in an opaque liquid such as muddy water. The observation target 30 has a recess 31, that is, an upwardly protruding inner surface 32. Since the opaque liquid exists in the recess 31, an observation is not easy. Therefore, in the present embodiment, the inner surface 32 of the recess 31 is observed as follows.

Figure 12A:
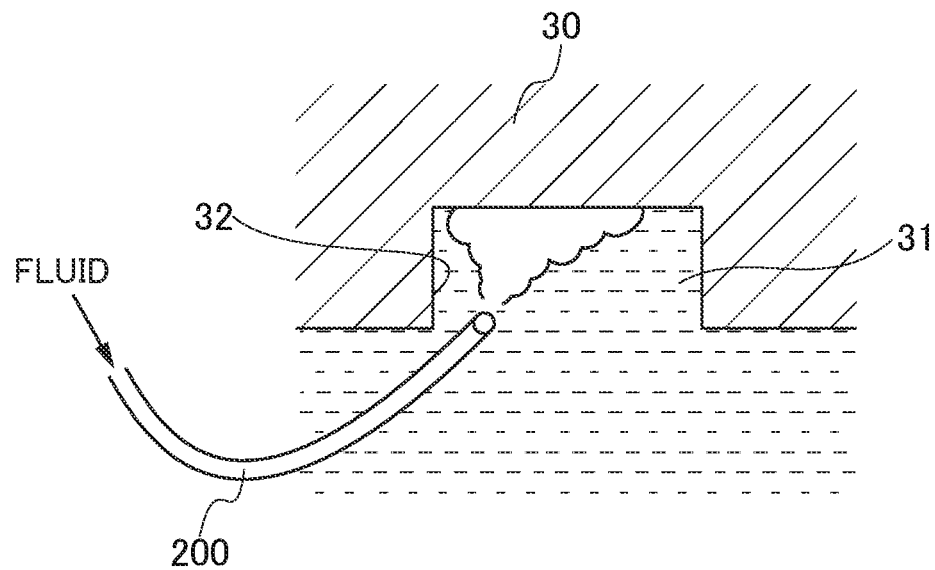
FIG. 12A is a view schematically illustrating a state of observing an observation target using an observation device 200.
Figure 12B:
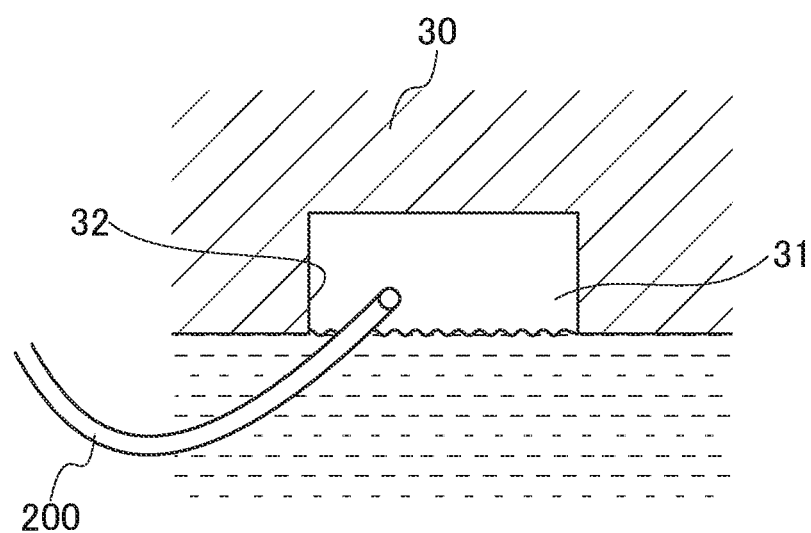
FIG. 12B is a view schematically illustrating a state of observing an observation target using the observation device 200.

FIGS. 12A and 12B are views schematically illustrating states of observing an observation target using an observation device 200. The observation device 200 is an endoscope with an air supply tube, and is provided with an imaging device at a distal end and can inject a fluid from the distal end. The fluid is favorably a gas (such as air) that is difficult to diffuse, but it may be a clean liquid. Note that "clean" means that at least the liquid has a higher degree of transparency than the opaque liquid existing around the observation target 30.

First, as illustrated in FIG. 12A, the observation device 200 injects the fluid into the recess 31. As a result, as illustrated in FIG. 12B, the opaque liquid is removed and the fluid is stored in the recess 31. In this state, a surface of the observation target 30, more specifically, the inner surface 32 of the recess 31 can be observed by an imaging device.

Note that, as an observation device, an underwater robot provided with an imaging device may be used. In this case, air may be injected as the fluid from an air tank mounted on the underwater robot. Alternatively, the air supply tube and the imaging device may be separately provided, and first the fluid may be injected through the air supply tube and then an observation may be performed with the imaging device.

As described above, in the present embodiment, the fluid is stored in the recess 31, and thus the observation target can be observed even in an opaque liquid.

Fifth Embodiment

Figure 13:
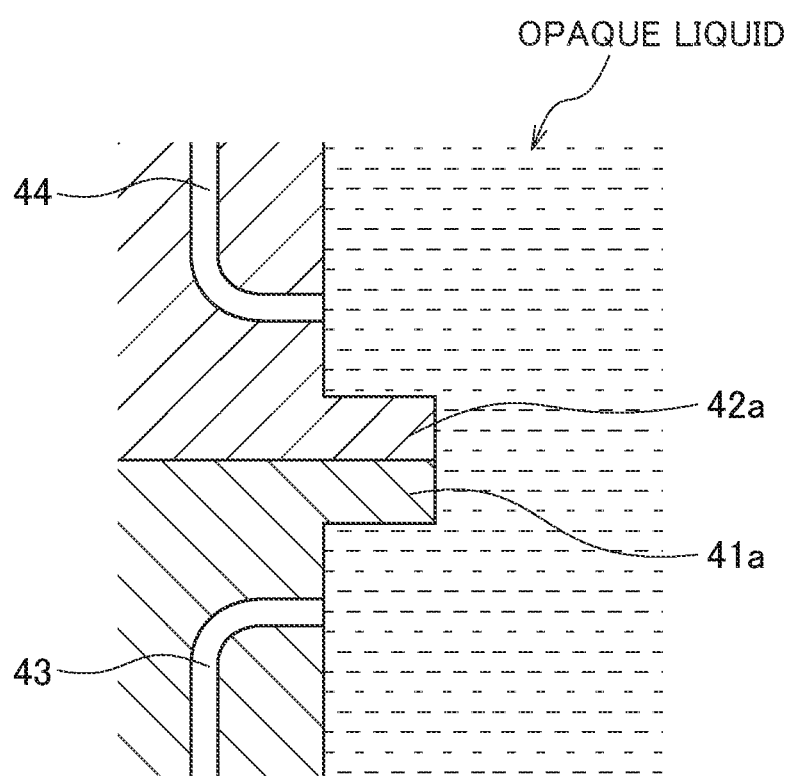
FIG. 13 is an enlarged sectional view of a vicinity of flanges 41a and 42a that are an example of an observation target in a fifth embodiment.

A fifth embodiment to be described next relates to injecting a fluid from an observation target and performing an observation FIG. 13 is an enlarged sectional view of a vicinity of flanges 41a and 42a that are an example of an observation target in the fifth embodiment. As a specific example, the observation target is the flanges 41a and 42a of pump suction piping installed in the seawater. Since an opaque liquid exists around the flanges 41a and 42a, an observation of the flanges 41a and 42a is not easy. Therefore, the present embodiment is configured as follows.

The observation target in the present embodiment includes fluid piping 43 provided on the flange 41a side and fluid piping 44 provided on the flange 42a side. The fluid piping 43 causes the fluid to be injected from below the flange 41a. The fluid piping 44 causes the fluid to be injected from above the flange 42a. The fluid to be injected may be clean water or a clean gas (air or the like). Further, the fluid from the fluid piping 43 and the fluid from the fluid piping 44 may be different from each other. Note that "clean" means that at least the liquid has a higher degree of transparency than the opaque liquid existing around the observation target.

Figure 14:
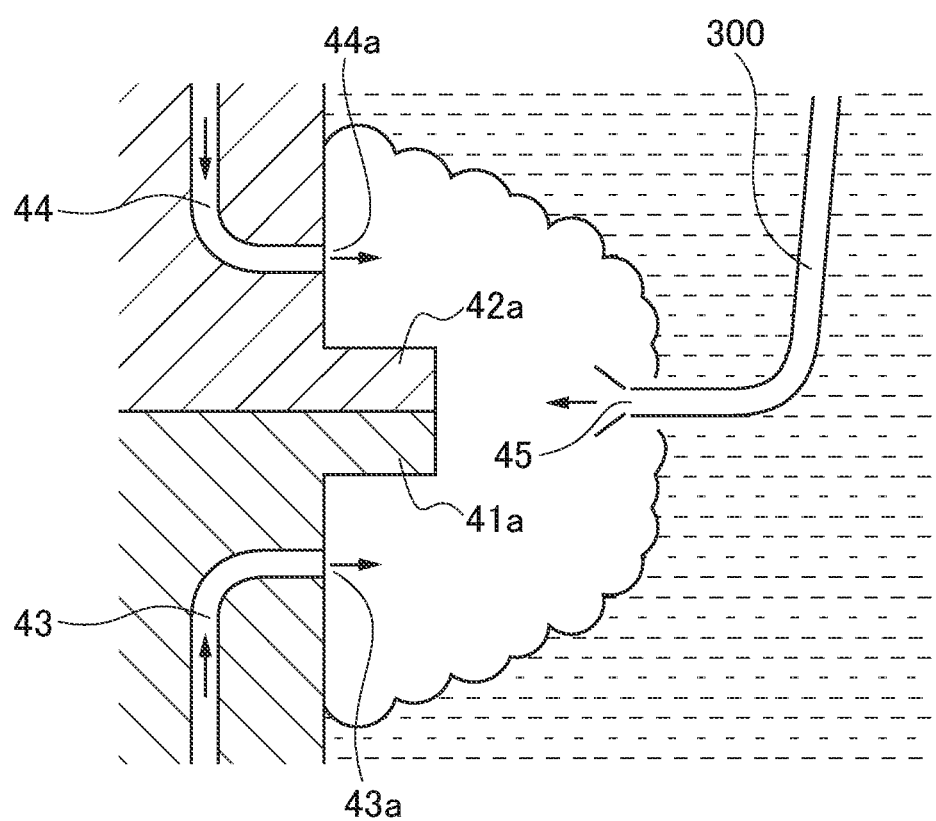
FIG. 14 is a view schematically illustrating a state of observing an observation target.

FIG. 14 is a view schematically illustrating a state of observing an observation target. First, an imaging device 45 provided in an observation device 300 such as an endoscope or an underwater robot is brought to face the flanges 41a and 42a. Then, a fluid is injected through injection ports 43a and 44a provided in tip ends of fluid piping 43 and 44. As a result, a clean fluid stays around the flanges 41a and 42a, more specifically, on an optical axis of the imaging device 45. In this state, the flanges 41a and 42a are observed by the imaging device 45.

As described above, in the present embodiment, the clean fluid stays between the flanges 41*a* and 42*a* as the observation target, and the imaging device 45, and therefore the observation target can be observed even in an opaque liquid.

Note that the observation target is not particularly limited, and the present embodiment can be applied to an arbitrary underwater machine. That is, in an underwater machine, when observing a certain place at a relatively high frequency by a periodic inspection or the like, the fluid injection port is provided in the vicinity of the observation target place. Then, the observation may be performed using the imaging device while injecting the fluid.

REFERENCE SIGNS LIST

11 Imaging device
11*a* Lens
11*b* Image processing system
12*a* to 12*c* Flow path
13 Filter
14 Pump
15 Injection member
16 Holding member
100 to 102 Observation device
2 Observation target
23 Base
24 Screw
25 Observation target
31 Recess
32 Inner surface
41*a*, 42*a* Flange
43, 44 Fluid piping
43*a*, 44*a* Injection port
60 Liquid supply source
(Third Aspect)

Technical Field

A third aspect relates to a pump inspection system including an endoscope to be inserted into a pump and an inspection device to which the endoscope is connected.

Background Art

There are various types of pumps. For example, for the purpose of transporting a liquid such as river water, a vertical pump is used. In the vertical pump, typically, a hanging pipe is installed on a pump installation floor above a suction water tank, and an impeller casing for accommodating an impeller is connected to a lower part of the hanging pipe. Since the vertical pump is operated in a state where the impeller and an underwater bearing are immersed in water, members constituting the vertical pump gradually wear as the operation time passes. In addition, corrosion may occur in the hanging pipe, the impeller casing, the impeller, and the like. For this reason, it is necessary to periodically perform internal inspection of the vertical pump, to grasp the wear situation and the occurrence of corrosion in the impeller, the impeller casing, and the like, and to repair or replace the members as necessary.

Therefore, various devices and methods for easy inspection of an interior of a pump have been conventionally proposed. For example, an inspection device including a rail horizontally arranged in a pump casing, an inspection port fixing tool for fixing the rail to an inspection port provided in the pump casing, an inner surface fixing tool for fixing the rail to an inner surface of the pump casing, an inspection unit movable in a horizontal manner on the rail has been proposed. The inspection port fixing tool is attached to one end of the rail, and the inner surface fixing tool is attached to the other end of the rail. The inspection unit is, for example, an endoscope for capturing an image of an interior of the pump casing, and is configured to be movable in the pump casing in an up and down direction (see Patent Literature 1).

[Outline of Third Aspect]
[Problem to be Solved by Third Aspect]

As described above, the endoscope can be moved in the pump in the up and down direction. Further, the endoscope is configured to be able to capture various directions by bending the distal end. However, in the conventional device, no consideration is given to knowing the position and direction of the endoscope in the pump, and it has been difficult to grasp which part of the pump is captured from which direction by the endoscope.

A third aspect of the present invention is to provide a pump inspection system capable of easily grasping which part of a pump is captured from which direction by an endoscope.

Solution to Problem

A pump inspection system of the third aspect is a pump inspection system including an endoscope inserted into a pump, and an inspection device to which the endoscope is connected, wherein the endoscope comprises: a capture module including a plurality of cameras, and a cable module configured to transmit camera images obtained by the plurality of cameras to the inspection device, and the inspection device comprises: a position determiner that determines a position of a distal end of the endoscope in the pump on the basis of camera images of an inside of the pump obtained by the plurality of cameras, and a direction determiner that determines a direction into which the distal end of the endoscope faces in the pump on the basis of the camera images of an inside of the pump obtained by the plurality of cameras.

According to this configuration, the position of the distal end of the endoscope in the pump and the direction in which the distal end of the endoscope faces can be obtained on the basis of the camera images of an inside of the pump captured by the plurality of cameras. Therefore, which part in the pump being captured from which direction by the endoscope can be easily grasped.

Further, in the pump inspection system according to the third aspect, the plurality of cameras may be arranged at different positions in the capture module to respectively obtain camera images of different capturing directions from one another, the inspection device may include a storage in which, for each of a plurality of reference markers provided inside the pump, a position of the reference marker in the pump is stored, and the position determiner may calculate a distance from the distal end of the endoscope to the reference marker on the basis of two camera images that capture the same reference marker, among the camera images of an inside of the pump obtained by the plurality of cameras, and may determine the position of the distal end of the endoscope in the pump on the basis of distances to at least three different reference markers and the positions of the reference markers in the pump.

According to this configuration, the distance from the distal end of the endoscope to the reference marker can be calculated on the basis of the two camera images obtained by capturing the same reference marker, of the camera images of an inside of the pump captured the plurality of cameras.

Then, the position (three-dimensional coordinates) of the distal end of the endoscope in the pump can be obtained on the basis of the distances to at least three different reference markers and the positions of the reference markers in the pump.

Further, in the pump inspection system according to the third aspect, directional relationships between the capturing directions of the plurality of cameras and a direction of the distal end of the endoscope may be stored in the storage, and the direction determiner may calculate the capturing direction of the camera that has captured the reference marker on the basis of an in-image position of the reference marker in the camera image that captures the reference marker, among the camera images of an inside of the pump obtained by the plurality of cameras, and may obtain the direction into which the distal end of the endoscope faces on the basis of the directional relationship between the direction of the distal end of the endoscope and the capturing direction of the camera.

According to this configuration, the capturing direction of the camera that has captured the reference marker can be calculated on the basis of the position (in-image position) of the reference marker in the camera image that captures the reference marker, of the camera images of an inside of the pump captured the plurality of cameras.

Then, the direction in which the distal end of the endoscope faces can be obtained from the directional relationship between the direction of the distal end of the endoscope and the capturing direction of the camera.

Further, in the pump inspection system according to the third aspect, the inspection device may include a multi-display that respectively displays the camera images of an inside of the pump obtained by the plurality of cameras on a plurality of screens.

According to this configuration, the camera images of parts in the pump captured by the plurality of cameras are displayed on the plurality of screens, and thus inspection of a plurality of places in the pump can be performed for each screen.

Further, in the pump inspection system according to the third aspect of the present invention, the inspection device may include a spherical display processor that converts the camera images of an inside of the pump obtained by the plurality of cameras into spherical display images, and a spherical display that displays the spherical display images on a spherical screen.

According to this configuration, the camera images of the inside of the pump captured by the plurality of cameras are converted into the spherical display images (for example, all-sky images) and displayed on the spherical screen (for example, an all-sky screen), and thus a state of the inside of the pump can be grasped in whole.

Further, in the pump inspection system according to the third aspect, the inspection device may include a stereoscopic display processor that converts the camera images of an inside of the pump obtained by the plurality of cameras into stereoscopic display images, and a stereoscopic display that displays the stereoscopic display images on a stereoscopic display screen.

According to this configuration, the camera images of the inside of the pump captured by the plurality of cameras are converted into the stereoscopic display images (three-dimensional images) and displayed on the stereoscopic display screen (a three-dimensional screen), and thus it is possible to stereoscopically (three-dimensionally) grasp a state of the inside of the pump.

[Effect of Third Aspect]

According to the third aspect, which part in the pump being captured from which direction by the endoscope can be easily grasped.

[Mode for Implementing Third Aspect]

Hereinafter, a pump inspection system according to an embodiment of the third aspect will be described with reference to the drawings. In the present embodiment, a case of a pump inspection system used for maintenance of a vertical pump or the like is exemplified. Note that reference numerals are assigned independently of the first and second aspects.

Figure 15:
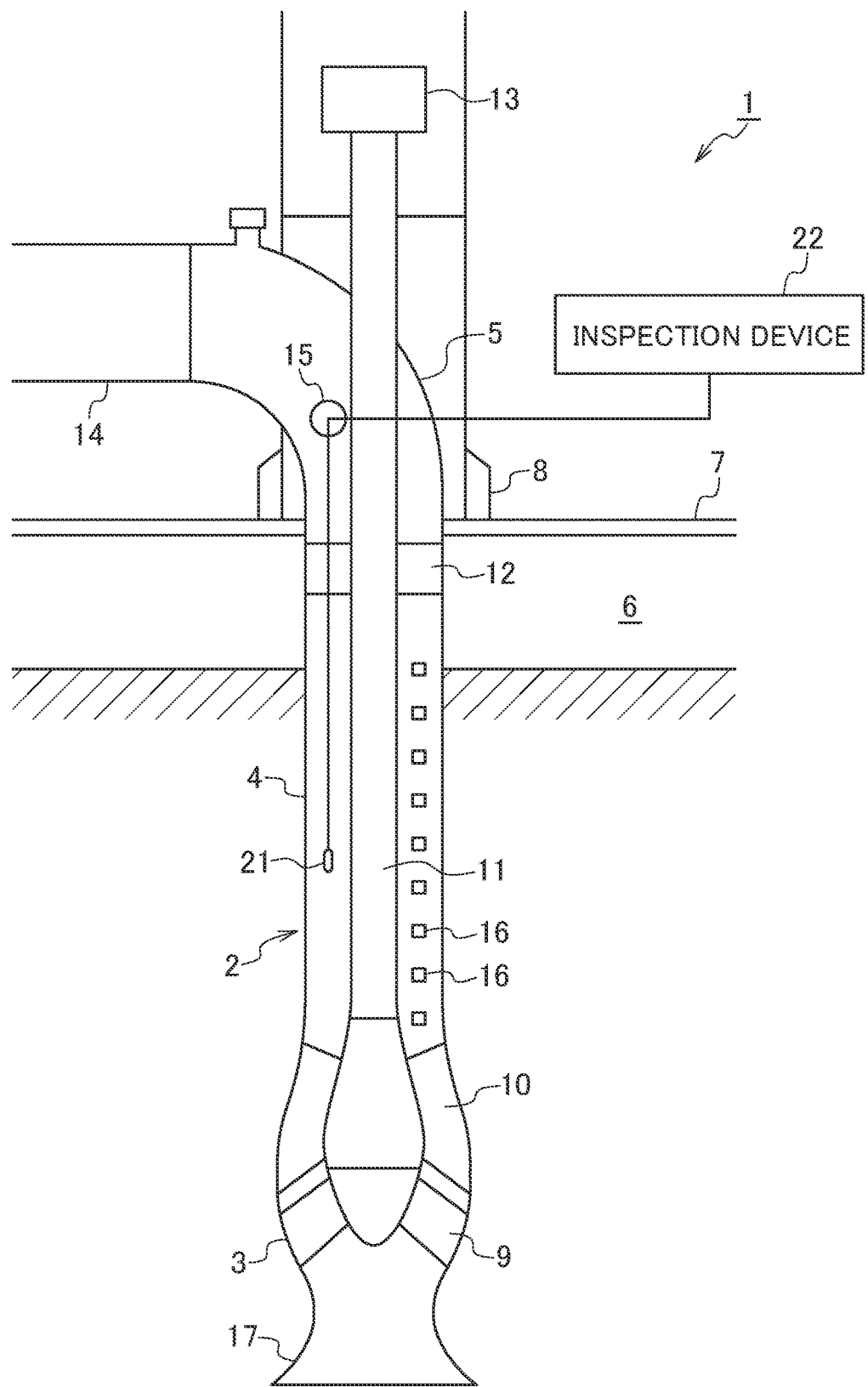
FIG. 15 is an explanatory view illustrating a configuration of a pump inspection system in an embodiment.

FIG. 15 is an explanatory view (sectional view) schematically illustrating an overall configuration of a vertical pump. As illustrated in FIG. 15, a pump casing 2 of a vertical pump 1 includes an impeller casing 3, a hanging pipe 4, and a discharge curved pipe 5. The impeller casing 3 is hung in a suction water tank 6 by the hanging pipe 4. The discharge curved pipe 5 is connected to an upper end of the hanging pipe 4. The pump casing 2 is fixed to a pump installation floor 7 above a suction water tank 6 via an installation base 8.

A suction bell mouth 17 opening downward is connected to a lower end of the impeller casing 3. An impeller 9 is housed inside the impeller casing 3. Above the impeller 9, a plurality of guide vanes 10 is provided. The guide vanes 10 are fixed to an inner peripheral surface of the impeller casing 3.

The impeller 9 is fixed to a rotating shaft 11 (main shaft), and the impeller 9 and the rotating shaft 11 are integrally rotated. The rotating shaft 11 extends in a vertical direction and is rotatably supported by an intermediate bearing 12. The rotating shaft 11 protrudes upward from the discharge curved pipe 5 and is connected to a drive source 13. When the impeller 9 is rotated through the rotating shaft 11 by operating the drive source 13, water (such as water drawn from a river) in the suction water tank 6 is sucked through the suction bell mouth 17, passes through the impeller casing 3, the hanging pipe 4, and the discharge curved pipe 5, and is transferred to the discharge pipe 14.

The discharge curved pipe 5 is provided with an inspection port 15 (hand hole) above an inspection point. The inspection point is, for example, a gap in the guide vane 10 or the impeller 9. An endoscope 21 (described below) is inserted into the pump casing 2 through the inspection port 15, and the vertical pump 1 is inspected. A plurality of reference markers 16 is provided on an inner surface (for example, an inner surface in the vicinity of the inspection point) of the pump casing 2. The reference marker 16 is identification information (for example, a letter, a number, a figure, or the like) for identifying the position where the reference marker 16 is provided (a position in the pump casing 2).

Next, a configuration of a pump inspection system 20 to be used for an inspection of the vertical pump 1 will be described with reference to the drawings. The pump inspection system 20 includes the endoscope 21 to be inserted into the pump casing 2 and an inspection device 22 to which the endoscope 21 is connected.

Figure 16:
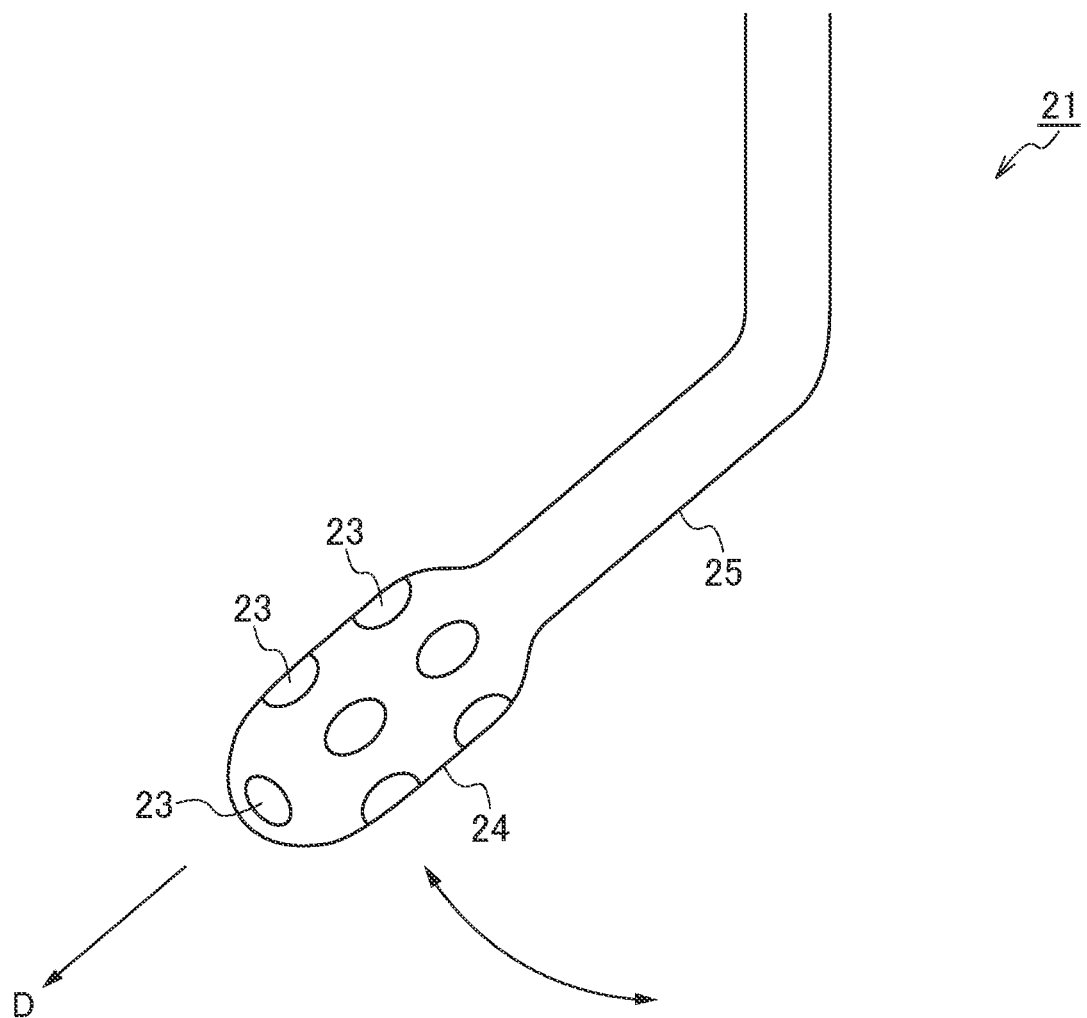
FIG. 16 is an explanatory view illustrating a configuration of an endoscope in an embodiment.

FIG. 16 is an explanatory view illustrating a configuration of the endoscope 21. As illustrated in FIG. 16, at the distal end of the endoscope 21, a capture module 24 including a plurality of cameras 23 (a camera A, a camera B, . . . ) is provided. A cable module 25 for transmitting camera images captured by the plurality of cameras 23 to the inspection device 22 is extended from the capture module 24. In this case, the plurality of cameras 23 is arranged at different positions of the capture module 24 so as to respectively capture camera images in different capturing directions. For example, the camera 23 for capturing the front is arranged on a front surface of the capture module 24, and the cameras 23 for capturing a diagonally forward side, a side, a diagonally rearward side, and the like are arranged on a side surface of the capture module 24. In addition, the cable module 25 has flexibility and can be arbitrarily bent. By bending the cable module 25, the direction of the capture module 24 (the direction in which the distal end of the endoscope 21 faces) can be changed.

Figure 17:
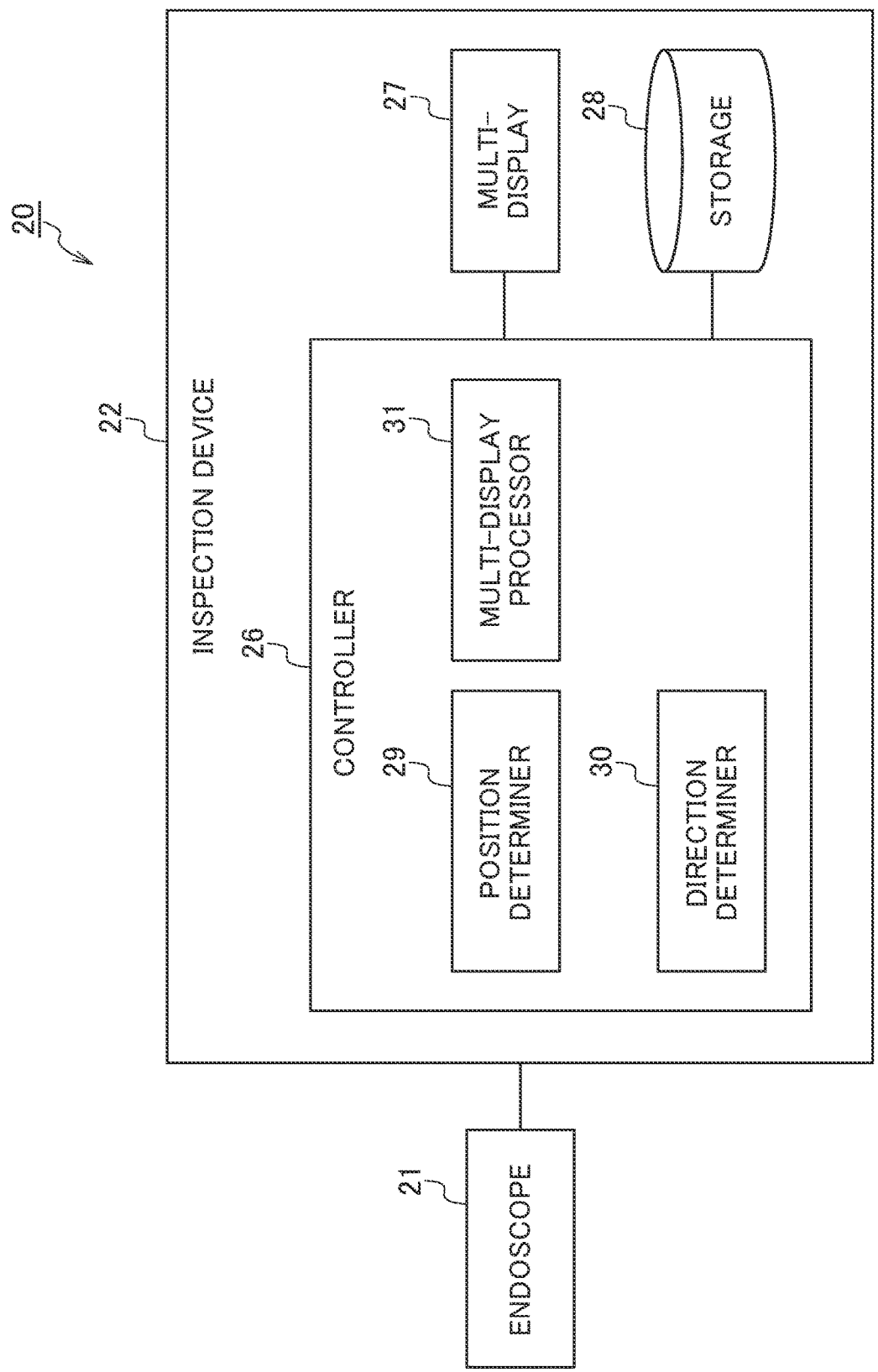
FIG. 17 is a block diagram illustrating a configuration of an inspection device according to an embodiment.

FIG. 17 is a block diagram illustrating a configuration of the inspection device 22. As illustrated in FIG. 17, the inspection device 22 includes a control module 26 including a CPU and the like, a multi-display 27 including a plurality of screens (a monitor A, a monitor B, . . . ), and a storage 28 including a memory and the like.

In the storage 28, the position of the reference marker 16 in the pump casing 2 is stored for each of the plurality of reference markers 16 (the reference marker A, the reference marker B, . . . ) provided on the inner surface of the pump casing 2. For example, coordinates $(X_A, Y_A, Z_A)$ of the reference marker A, coordinates $(X_B, Y_B, Z_B)$ of the reference marker B, . . . are stored. Note that $(X, Y, Z)$ are three coordinates in an orthogonal linear coordinate system.

Further, in the storage 28, a directional relationship between the capturing direction of each of the plurality of cameras 23 and the direction of the distal end (reference direction) of the endoscope 21 is stored. For example, an angle $(\theta_A, \varphi_A)$ of the camera A in the capturing direction with respect to the direction of the distal end (reference direction) of the endoscope 21, an angle $(\theta_B, \varphi_B)$ of the camera B in the capturing direction with respect to the direction of the distal end (reference direction) of the endoscope 21, . . . and stored. Note that $(\theta, \varphi)$ are two angular coordinates of a spherical coordinate system.

The control module 26 includes a position determiner 29, a direction determiner 30, and a multi-display processor 31. The position determiner 29 has a function to obtain the position of the distal end of the endoscope 21 in the pump casing 2 on the basis of the camera images of an inside of the pump casing 2 captured by the plurality of cameras 23. More specifically, the position determiner 29 calculates a distance from the distal end of the endoscope 21 to the reference marker 16 on the basis of two camera images that capture the same reference marker 16, of the camera images of an inside of the pump casing 2 captured by the plurality of cameras 23, and obtains the position of the distal end of the endoscope 21 in the pump casing 2 on the basis of distances to at least three different reference markers 16 and the positions of the reference markers 16 in the pump casing 2.

Further, the direction determiner 30 has a function to obtain the direction in which of the distal end of the endoscope 21 faces in the pump casing 2 on the basis of the camera images of an inside of the pump casing 2 captured by the plurality of cameras 23. More specifically, the direction determiner 30 calculates the capturing direction of the camera 23 that has captured the reference marker 16 on the basis of the position (in-image position) of the reference marker 16 in the camera image that captures the reference marker 16, of the camera images of an inside of the pump casing 2 captured by the plurality of cameras 23, and obtains the direction in which the distal end of the endoscope 21 faces on the basis of the directional relationship between the direction of the distal end of the endoscope 21 and the capturing direction of the camera 23.

The multi-display 27 has a function to respectively display the camera images of an inside of the pump casing 2 captured by the plurality of cameras 23 (the camera A, the camera B, . . . ) on the plurality of screens (the monitor A, the monitor B, . . . ). For example, the camera image of an inside of the pump casing 2 captured by the camera A is displayed on the monitor A, and the camera image of an inside of the pump casing 2 captured by the camera B is displayed on the monitor B.

Note that the multi-display 27 does not necessarily need to display all the camera images on all the screens. For example, a part (for example, only an image in a predetermined horizontal direction) of the camera images may be displayed on a part (for example, only on the monitor A) of the screens. In the present embodiment, since the direction determiner 30 obtains the direction in which the distal end of the endoscope 21 faces, which camera image captures the predetermined horizontal direction is known. Therefore, the camera image that captures the predetermined horizontal direction (the camera image to be displayed on the screen) can be selected from the plurality of camera images.

According to the pump inspection system 20 of the present embodiment, the position of the distal end of the endoscope 21 in the pump casing 2 and the direction in which the distal end of the endoscope 21 faces can be obtained on the basis of the camera images of an inside of the pump casing 2 captured by the plurality of cameras 23. Therefore, which part of the pump casing 2 being captured from which direction by the endoscope 21 can be easily grasped.

In the present embodiment, the distance from the distal end of the endoscope 21 to the reference marker 16 can be calculated on the basis of the two camera images that capture the same reference marker 16, of the camera images of an inside of the pump casing 2 captured the plurality of cameras 23. Then, the position (three-dimensional coordinates) of the distal end of the endoscope 21 in the pump casing 2 can be obtained on the basis of the distances to at least three different reference markers 16 and the positions of the reference markers 16 in the pump casing 2.

Further, in the present embodiment, the capturing direction of the camera 23 that has captured the reference marker 16 can be calculated on the basis of the position (in-image position) of the reference marker 16 in the camera image that captures the reference marker 16, of the camera images of an inside of the pump casing 2 captured the plurality of cameras 23. Then, the direction in which the distal end of the endoscope 21 faces can be obtained from the directional relationship between the direction of the distal end of the endoscope 21 and the capturing direction of the camera 23.

In this case, the camera images of parts in the pump casing 2 captured by the plurality of cameras 23 (the camera A, the camera B, . . . ) are displayed on the plurality of screens (the monitor A, the monitor B, . . . ) of the multi-display 27. Therefore, inspection of a plurality of places in the pump casing 2 can be performed for each screen.

Although the embodiment of the third aspect has been described by way of example, the scope of the third aspect is not limited to the example, and changes and modifications can be made according to the purpose within the scope described in the claims.

For example, in the above-described embodiment, the inspection device includes the multi-display 27 that respectively displays the camera images of an inside of the pump casing 2 captured by the plurality of cameras 23 on the plurality of screens. However, the scope of the third aspect is not limited to the embodiment.

Figure 18:
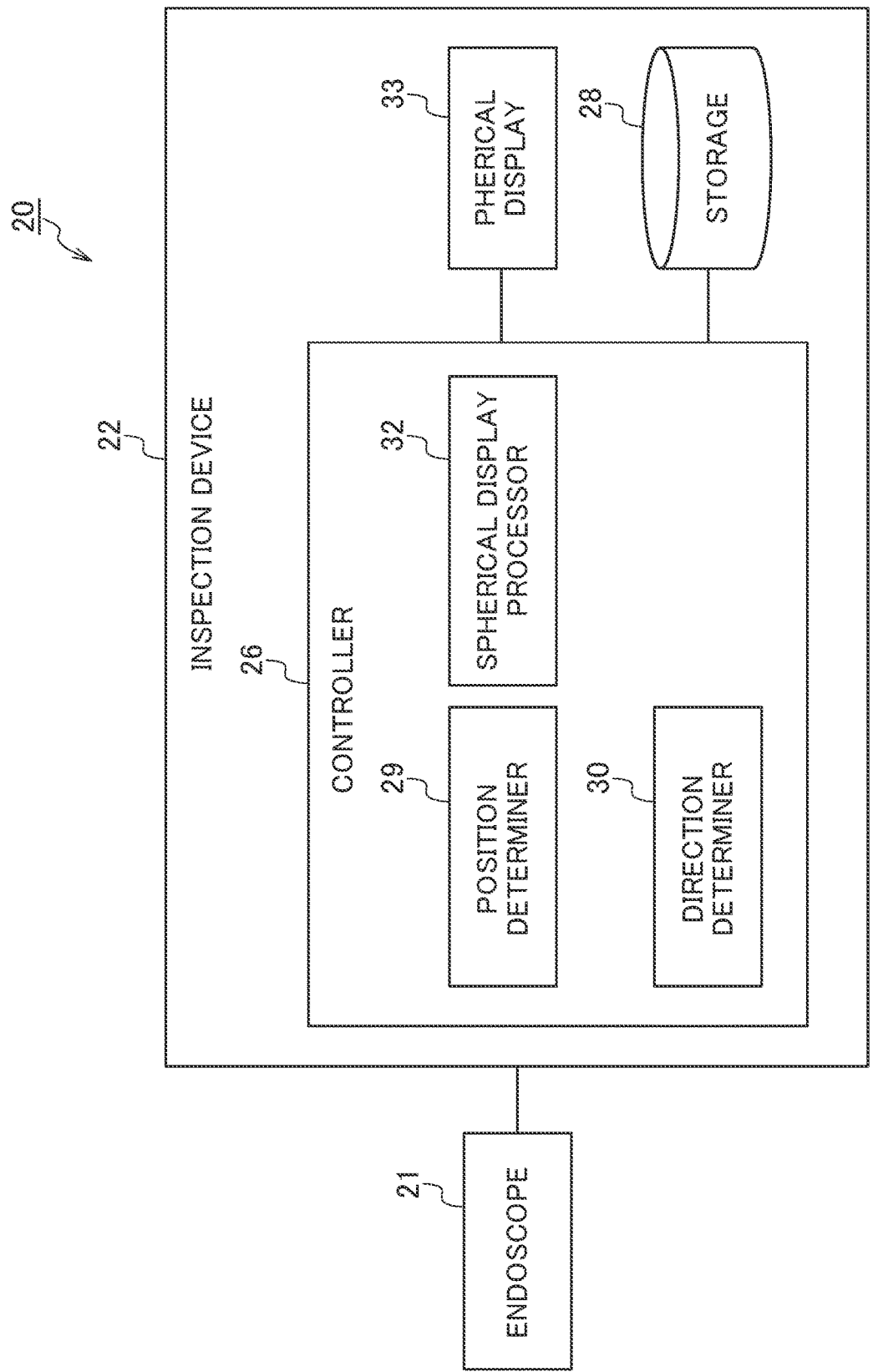
FIG. 18 is a block diagram illustrating a configuration of an inspection device according to another embodiment.

FIG. 18 illustrates another embodiment of an inspection device. As illustrated in FIG. 18, the inspection device may include a spherical display processor 32 that converts the camera images of an inside of the pump casing 2 captured by the plurality of cameras 23 into spherical display images, and a spherical display 33 that displays the spherical display images on a spherical screen. For example, the spherical display image is an all-sky image, and the spherical display 33 is an all-sky monitor. Note that the spherical display image may be a partial spherical image, and the spherical display 33 may be a partial spherical monitor.

According to this inspection device, the camera images of the inside of the pump casing 2 captured by the plurality of cameras 23 are converted into the spherical display images (for example, all-sky images) and displayed on the spherical screen (for example, an all-sky screen), and thus a state of the inside of the pump casing 2 can be grasped in whole.

Figure 19:
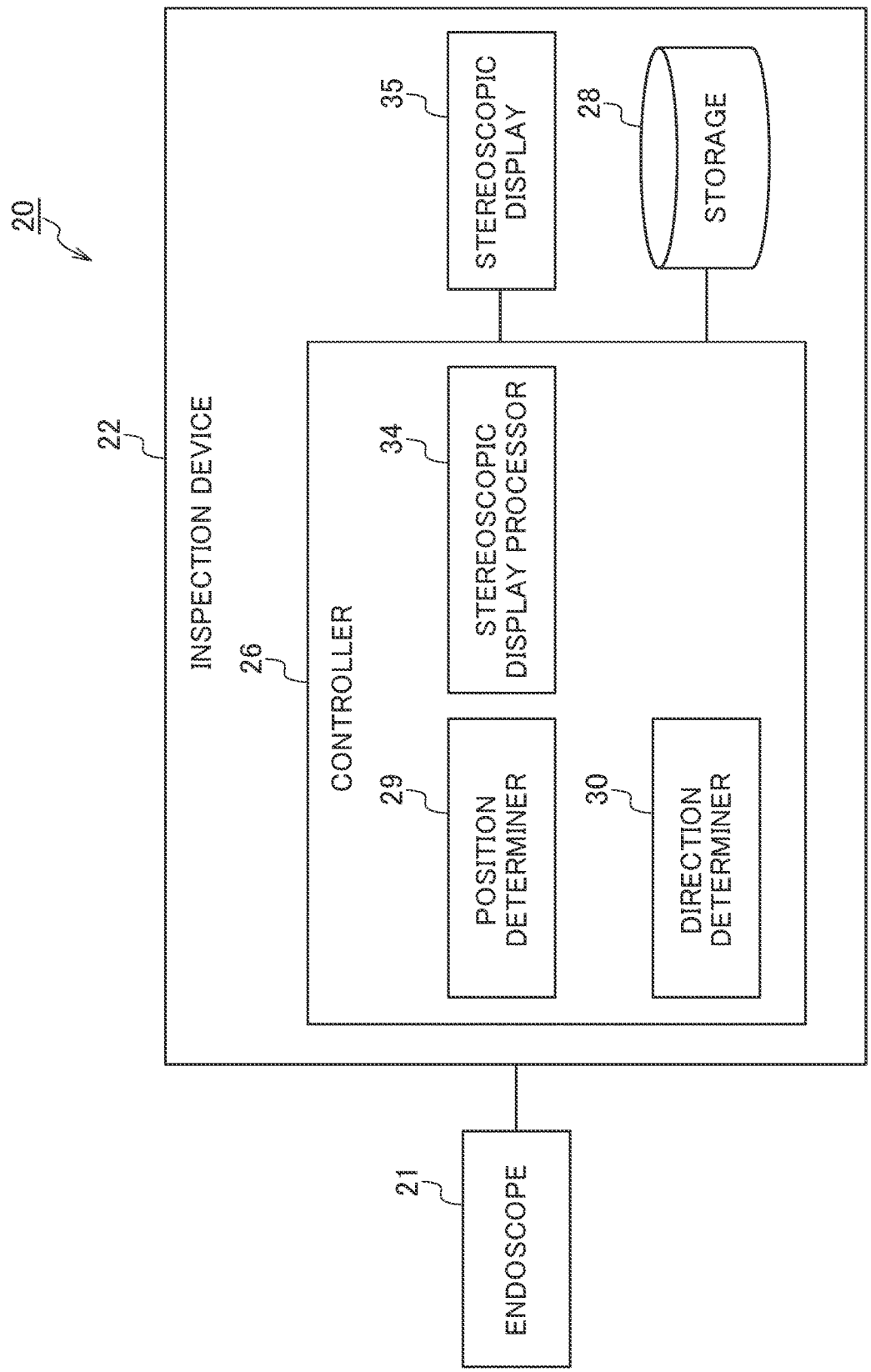
FIG. 19 is a block diagram illustrating a configuration of an inspection device according to another embodiment.

Further, FIG. 19 illustrates another embodiment of an inspection device. As illustrated in FIG. 19, the inspection device may include a stereoscopic display processor 34 that converts the camera images of an inside of the pump casing 2 captured by the plurality of cameras 23 into stereoscopic display images (three-dimensional display screen), and a stereoscopic display 35 that displays the stereoscopic display images on a stereoscopic display screen. Note that the stereoscopic display screen may be a naked-eye three-dimensional display screen or a glasses-based three-dimensional display screen.

According to such an inspection device, the camera images of the inside of the pump casing 2 captured by the plurality of cameras 23 are converted into the stereoscopic display images (three-dimensional images) and displayed on the stereoscopic display screen (a three-dimensional screen), and thus the state of the inside of the pump casing 2 can be stereoscopically (three-dimensionally) grasped.

Note that the reference marker 16 may be an asymmetric two-dimensional figure instead of a point. In this case, if information of the position, direction, and size of the two-dimensional figure on an object is stored in advance, the position and the direction of the endoscope 21 with respect to the object can be specified by an analysis of a captured image by simply capturing one reference marker 16 by one camera 23 having known optical characteristics. The two-dimensional figure may be an arbitrary figure, and may be a letter, a number, or the like. However, asymmetry is required, and thus "O", "o", "l" "I", "X", "x", and the like are not desirable in the alphabet, for example. However, such alphabets can be used by collapsing the symmetry by a combination of a plurality of alphabets. For example, "Xx" can be used. The camera 23 may be a monocular. However, by adopting the aforementioned system, the robustness and precision of positioning and determining the direction can be enhanced with the plurality of cameras 23. For example, in the case of a single camera 23, if all the reference markers 16 deviate from the field of view, the position and direction analysis becomes impossible. In the case of the plurality of cameras 23, the position and direction analysis becomes possible as long as one camera 23 can capture one reference marker 16.

INDUSTRIAL APPLICABILITY

As described above, the pump inspection system according to the third aspect has an effect to easily grasp which part in the pump is captured from which direction by the endoscope, and is used for maintenance of the vertical pump and the like and is useful.

REFERENCE SIGNS LIST

1 Vertical pump
2 Pump casing
3 Impeller casing
4 Hanging pipe
5 Discharge curved pipe
6 Suction water tank
7 Pump installation floor
8 Installation base
9 Impeller
10 Guide vane
11 Rotating shaft
12 Intermediate bearing
13 Drive source
14 Discharge piping
15 Inspection port
16 Reference marker
17 Suction bell mouth
20 Pump inspection system
21 Endoscope
22 Inspection device
23 Camera
24 Capture module
25 Cable module
26 Control module
27 Multi-display
28 Storage
29 Position determiner
30 Direction determiner
31 Multi-display processor
32 Spherical display processor
33 Spherical display
34 Stereoscopic display processor
35 Stereoscopic display
(Fourth Aspect)

Technical Field

A fourth aspect relates to an underwater robot control system and an underwater robot control method.

Background Art

Conventionally, a remotely operable underwater robot (for example, an underwater drone) is known (see, for example, Patent Literature 1).
[Outline of Fourth Aspect]
[Problem to be Solved by Fourth Aspect]

Use of a remote controllable underwater robot (for example, an underwater drone, or the like) is conceivable in various applications such as inspection of underwater machinery (for example, parts of a pump), underwater exploration, and the like. However, when using an underwater robot (for example, an underwater drone), there is a problem that the underwater moving device in water (in liquid) cannot be seen from an operator on land or on water and the remote operation may be difficult, in the presence of opaque or less transparent water such as muddy water and/or opaque chemicals and/or colored organisms (algae, plankton, or the like).

The fourth aspect of the present invention has been made in view of the above problem, and an objective is to provide an underwater robot control system and an underwater robot control method for facilitating remote control even in a case where an underwater robot in water cannot be seen from an operator.

Solution to Problem

An underwater robot control system according to the fourth aspect is an underwater robot control system of a remote control type, the underwater robot control system including an underwater robot capable of transmitting a sonic wave and including a propulsion mechanism, three or more communication buoys, each communication buoy capable of receiving the sonic wave transmitted by the underwater robot, capable of transmitting a reception time when the communication buoy has received the sonic wave, and configured to float on a water surface, a position detector configured to detect respective positions of the communication buoys, a communicator configured to receive the reception times transmitted by the communication buoys, and a position determiner configured to determine a position of the underwater robot, using differences between a transmission time of the sonic wave and the reception times when the communication buoys have received the sonic wave, and the respective positions of the communication buoys.

According to this configuration, the operator can grasp the position of the underwater robot even in the case where the underwater robot in water cannot be seen from the operator, and thus the remote control can be facilitated.

The underwater robot control system according to the fourth aspect is the underwater robot control system according to a first aspect, wherein the position determiner determines a distance between each of the communication buoys and the underwater robot, using the differences between the transmission time of the sonic wave and the reception times when the respective communication buoys have received the sonic wave, and determines the position of the underwater robot on the basis of the determined distances and the respective positions of the communication buoys.

According to this configuration, the position of the underwater robot can be determined even in the case where the underwater robot in water cannot be seen from the operator.

The underwater robot control system according to the fourth aspect is the underwater robot control system according to the first or second aspect, wherein the position determiner moves the underwater robot by a predetermined distance and stops the underwater robot, after the stop, determines a position of the underwater robot after stop, using the differences between the transmission time of the sonic wave and the reception times when the communication buoys have received the sonic wave, and the respective positions of the communication buoys, and determines a direction of the underwater robot, using the positions of the underwater robots before and after movement.

According to this configuration, the direction of the underwater robot can be determined even in the case where the underwater robot in water cannot be seen from the operator.

The underwater robot control system according to the fourth aspect is the underwater robot control system according to a third aspect, wherein the underwater robot is capable of performing imaging underwater, and the position determiner changes the direction of the underwater robot toward an inspection target, using the direction of the underwater robot.

According to this configuration, the underwater robot can be moved toward the inspection target, and the inspection target can be inspected with the image that has imaged the inspection target after movement even in the case where the underwater robot in water cannot be seen from the operator.

The underwater robot control system according to the fourth aspect is the underwater robot control system according to any one of first to fourth aspects, wherein the position detector is a positioner provided in each of the communication buoys, and which measures the position of the communication buoy.

According to this configuration, the position of the communication buoy can be measured.

The underwater robot control system according to the fourth aspect is an underwater robot control system of a remote control type, the underwater robot control system including an underwater robot capable of imaging an inspection target placed in water and including a propulsion mechanism, a communication buoy including a sonar capable of transmitting an ultrasonic wave and capable of capturing a reflection wave of the ultrasonic wave, and configured to float on a water surface, a position detector configured to detect a position of the communication buoy, and a position determiner configured to determine a position of the underwater robot, using an observation result by the sonar and the position of the communication buoy.

According to this configuration, the operator can grasp the position of the underwater robot even in the case where the underwater robot in water cannot be seen from the operator, and thus the remote control can be facilitated.

The underwater robot control system according to the fourth aspect is the underwater robot control system according to a sixth aspect, further including a control module configured to control the underwater robot to make a difference between the position of the underwater robot and a position on a locus from the underwater robot to the inspection target minimum According to this configuration, the control module can guide the underwater robot to a destination by continuing the control.

The underwater robot control system according to the fourth aspect is the underwater robot control system according to a sixth or seventh aspect, wherein the position detector is a positioner provided in each of the communication buoys, and which measures the position of the communication buoy.

According to this configuration, the position of the communication buoy can be measured.

The underwater robot control system according to the fourth aspect is an underwater robot control system of a remote control type, the underwater robot control system including an underwater robot capable of imaging an inspection target placed in water and including a propulsion mechanism, and a communication buoy configured to float on a water surface, wherein the communication buoy includes a floating member that floats on water, a sonic transmitter capable of transmitting a sonic wave and receiving a sonic wave reflected from the underwater robot, a processor configured to generate image data using the sonic wave received by the sonic transmitter, and a communicator configured to transmit an image signal including the generated image data.

According to this configuration, the operator can grasp the positional relationship between the underwater robot and the inspection target from the image data even in the case where the underwater robot in water cannot be seen from the operator, and thus the remote control can be facilitated.

The underwater robot control system according to the fourth aspect is the underwater robot control system according to a ninth aspect, wherein the sonic transmitter is a synthetic aperture sonar capable of transmitting a sonic wave in a plurality of directions.

According to this configuration, sonar images in a plurality of directions can be acquired at a time, and the possibility of acquiring a sonar image of the underwater robot can be improved regardless of the azimuth of the underwater robot.

The underwater robot control system according to the fourth aspect is the underwater robot control system according to the ninth aspect, wherein the sonic transmitter is a synthetic aperture sonar capable of transmitting a sonic wave in one direction, and the communication buoy includes a driver that rotates the synthetic aperture sonar.

According to this configuration, the synthetic aperture sonar can be rotated to perform scanning, and sonar images in a plurality of direction can be acquired. Therefore, a sonar image of the underwater robot can be acquired regardless of the direction of the underwater robot.

The underwater robot control system according to the fourth aspect is the underwater robot control system according to the ninth aspect, wherein the sonic transmitter is a transducer, and the communication buoy includes a driver that moves the transducer up and down.

According to this configuration, the transducer can be moved up and down to perform scanning, and a sonar image in a depth direction can be acquired. Therefore, a sonar image of the underwater robot can be acquired regardless of the depth in water of the underwater robot.

The underwater robot control system according to the fourth aspect is the underwater robot control system according to the ninth aspect, wherein the sonic transmitter is a transducer array in which a plurality of transducers is arranged in an approximately planar manner.

According to this configuration, the transducer array can be rotated to perform scanning, and a sonar image in a predetermined range in the depth direction can be acquired at a time. Therefore, a sonar image including the underwater robot can be easily acquired.

The underwater robot control system according to the fourth aspect is an underwater robot control system of a remote control type, the underwater robot control system including an underwater robot including an acoustic camera that captures an underwater picture with an ultrasonic wave and generates image data, and a communicator that transmits the image data, and including a propulsion mechanism, a display device, and a controller configured to receive the image data and display the image data on the display device, wherein the controller controls the underwater robot to be moved according to an operation by an operator.

According to this configuration, the operator can bring the underwater robot close to the inspection target while watching the image data displayed on the display device.

An underwater robot control method according to the fourth aspect is an underwater robot control method of a remote control type, the underwater robot control method including the steps of capturing an underwater picture with an ultrasonic wave and generating image data, by an underwater robot, transmitting the image data, by an underwater robot, receiving the image data, by the controller, displaying the image data on a display device, by the controller, and controlling the underwater robot to be moved according to an operation by an operator, by the controller.

According to this configuration, the operator can bring the underwater robot close to the inspection target while watching the image data displayed on the display device.

An underwater robot control method according to the fourth aspect is an underwater robot control method of a remote control type, the underwater robot control method including the steps of moving an underwater robot on a water surface according to an operation by an operator, by a controller, submerging the underwater robot in water according to an operation by an operator, by the controller, in a case where the underwater robot is moved near an inspection target, imaging an inspection portion of the inspection target in water, by the underwater robot, transmitting image data generated by the imaging to the controller, by the underwater robot, and displaying the image data on a display device, by the controller.

According to this configuration, the underwater robot can be moved to the inspection portion in water and can image and display the inspection portion to inspect the inspection portion even in a case where the underwater robot in water cannot be visually confirmed from the operator.

[Effect of Fourth Aspect]

According to the fourth aspect, the operator can grasp the position of the underwater robot even in the case where the underwater robot in water cannot be seen from the operator, and thus the remote control can be facilitated.

[Mode for Implementing Fourth Aspect]

Hereinafter, embodiments will be described with reference to the drawings. Note that, in the drawings attached to the present specification, the scales, the dimensional ratios in the vertical and horizontal directions, and the like are changed and exaggerated as appropriate from actual values for convenience of easy understanding of the drawings. Note that reference numerals are assigned independently of the first, second, and third aspects.

First Embodiment

Figure 20:
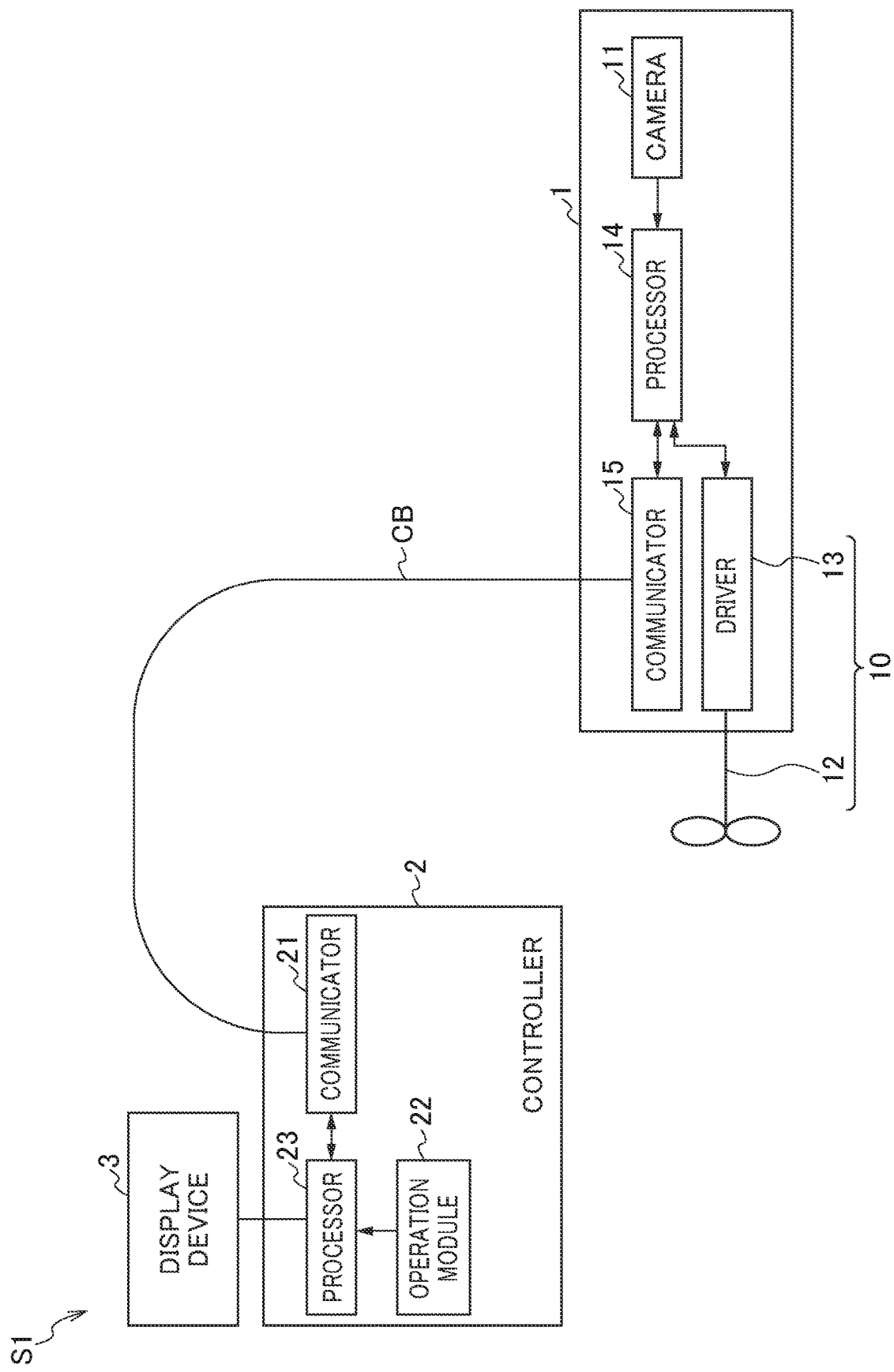
FIG. 20 is a block diagram illustrating a schematic configuration of an underwater robot control system according to a first embodiment.

FIG. 20 is a block diagram illustrating a schematic configuration of an underwater robot control system according to a first embodiment. As illustrated in FIG. 20, an underwater robot control system S1 includes an underwater robot 1 movable in water, a controller 2 for operating the underwater robot 1 from a remote place (for example, on water, on land, etc.), and a display device 3 for displaying a picture captured by the underwater robot 1. Here, the picture includes both moving images and still images. The underwater robot 1 is, for example, an underwater drone. In the following embodiments, description will be given on the assumption that the underwater robot 1 is an underwater drone as an example.

The underwater robot 1 includes a camera 11, a propulsion mechanism 10, a processor 14, and a communicator 15. Here, the propulsion mechanism 10 according to the present embodiment includes a propeller 12 and a driver 13 connected to the propeller, as an example. The processor 14 is connected to the camera 11, the driver 13, and the communicator 15 via a bus.

The camera 11 images an object in water and generates image data. The camera 11 includes an image sensor that images the object and generates the image data, and a lens unit that focuses light from the object on the image sensor.

The driver 13 rotates the propeller 12. The driver 13 is, for example, a motor. The processor 14 controls the driver 13 to adjust the rotation amount and/or the rotating direction of the propeller 12. With the control, the underwater robot 1 can move forward and backward.

The communicator 15 is connected to the controller 2 via a communication cable CB. With the configuration, the communicator 15 can communicate with the controller 2.

The processor 14 causes the communicator 15 to transmit the image data obtained by the camera to the controller 2. Note that, in this embodiment, the description will be given on the assumption that the communicator 15 and a communicator 21 of the controller 2 perform communication by wired means, as an example. However, the present embodiment is not limited thereto, and may perform communication by wireless means (radio wave, optical communication, or ultrasonic communication).

The controller 2 includes a communicator 21, an operation module 22, and a processor 23. The processor 23 is connected to the communicator 21 and the operation module 22 via a bus.

The communicator 21 receives the image data transmitted from the communicator 15 of the underwater robot 1. The processor 23 performs control to display the image data on the display device 3.

The operation module 22 receives an operation for operating the underwater robot 1 from the operator. The operation module 22 is, for example, a control stick.

The processor 23 generates a control signal for moving the underwater robot 1 in response to the operation received by the operation module 22, and causes the communicator 21 to transmit the control signal to the underwater robot 1. As a result, the communicator 15 of the underwater robot 1 receives this control signal, and the processor 14 of the underwater robot 1 controls the driver 13 to move the underwater robot 1 on the basis of the control signal.

Figure 21:
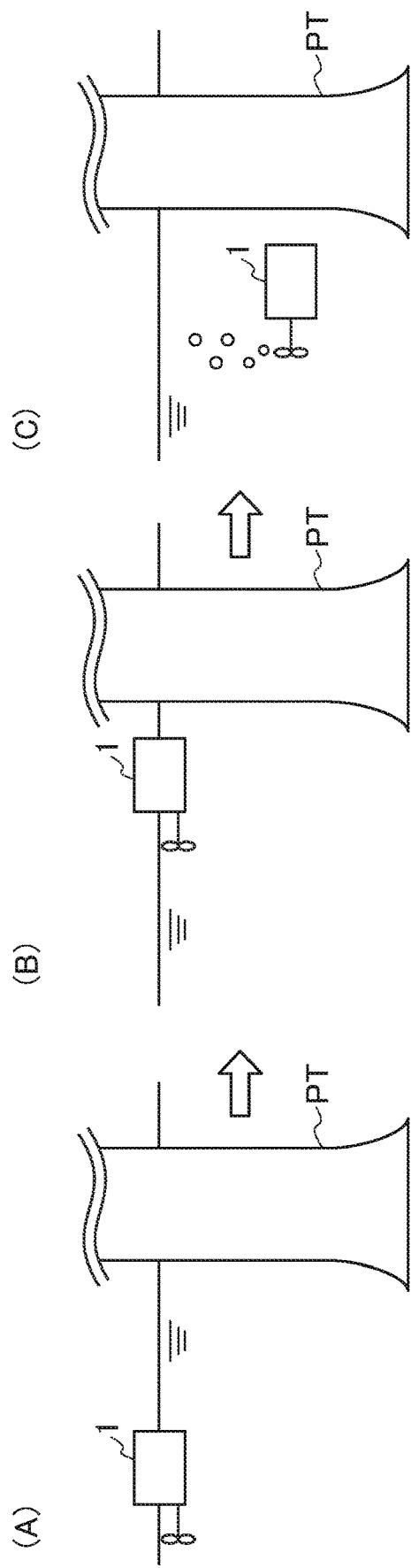
FIG. 21 is a diagram for describing an underwater robot control method according to the first embodiment.

FIG. 21 is a diagram for describing an underwater robot control method according to the first embodiment. FIG. 21 illustrates an underwater robot control method used when the underwater robot in water cannot be visually confirmed due to an influence of the presence of opaque or less transparent water such as muddy water and/or opaque chemicals and/or colored organisms (algae, plankton, or the like). The present embodiment will be described on the assumption that a suction water tank is filled with muddy water, and an inspection portion can be visualized by optical capturing when approaching the inspection portion, as an example. The opaque in the present embodiment means the degree of transparency in which the inspection portion can be visualized by optical capturing when approaching the inspection portion.

As illustrated in FIG. 21(A), the underwater robot 1 is moved on a water surface towards a pumping pipe PT of the pump. At this time, since the underwater robot 1 moves on water, the operator can operate the underwater robot 1 while visually confirming the position of the underwater robot 1. When the operator visually confirms that the underwater robot 1 has approached the pumping pipe PT of the pump, as illustrated in FIG. 21(B), the processor 23 controls the underwater robot 1 to submerge along the pumping pipe PT of the pump, as illustrated in FIG. 21(C), according to the operation by the operator. During the submerging, the image data of the pumping pipe P imaged by the camera 11 of the underwater robot 1 is displayed on the display device 3. Therefore, the operator can move the underwater robot 1 to the inspection portion of the pumping pipe P as an inspection target by submerging the underwater robot 1 while watching the image data.

Then, when the underwater robot 1 has reached the inspection portion, the underwater robot 1 images the inspection portion of the pump in water. Then, the underwater robot 1 transmits the imaged and generated image data to the controller 2. The controller 2 displays the image data on the display device 3.

As described above, the underwater robot control method of a remote control type according to the first embodiment includes the step of moving, by the controller 2, the underwater robot 1 on the water surface according to the operation by the operator. Further, the underwater robot control method includes the step of submerging, by the controller 2, the underwater robot 1 in water according to the operation of the operator, when the underwater robot 1 has moved near the pumping pipe PT. The underwater robot control method includes the step of imaging, by the underwater robot 1, the inspection portion of the inspection target (here, the pumping pipe of the pump, as an example), the step of transmitting, by the underwater robot 1, the imaged and generated image data to the controller 2, and the step of displaying, by the controller 2, the image data on the display device 3.

With this configuration, the underwater robot 1 can be moved to the inspection portion in water and can image the inspection portion to inspect the inspection portion even in a case where the underwater robot 1 in water cannot be visually confirmed from the operator.

Second Embodiment

Figure 22:
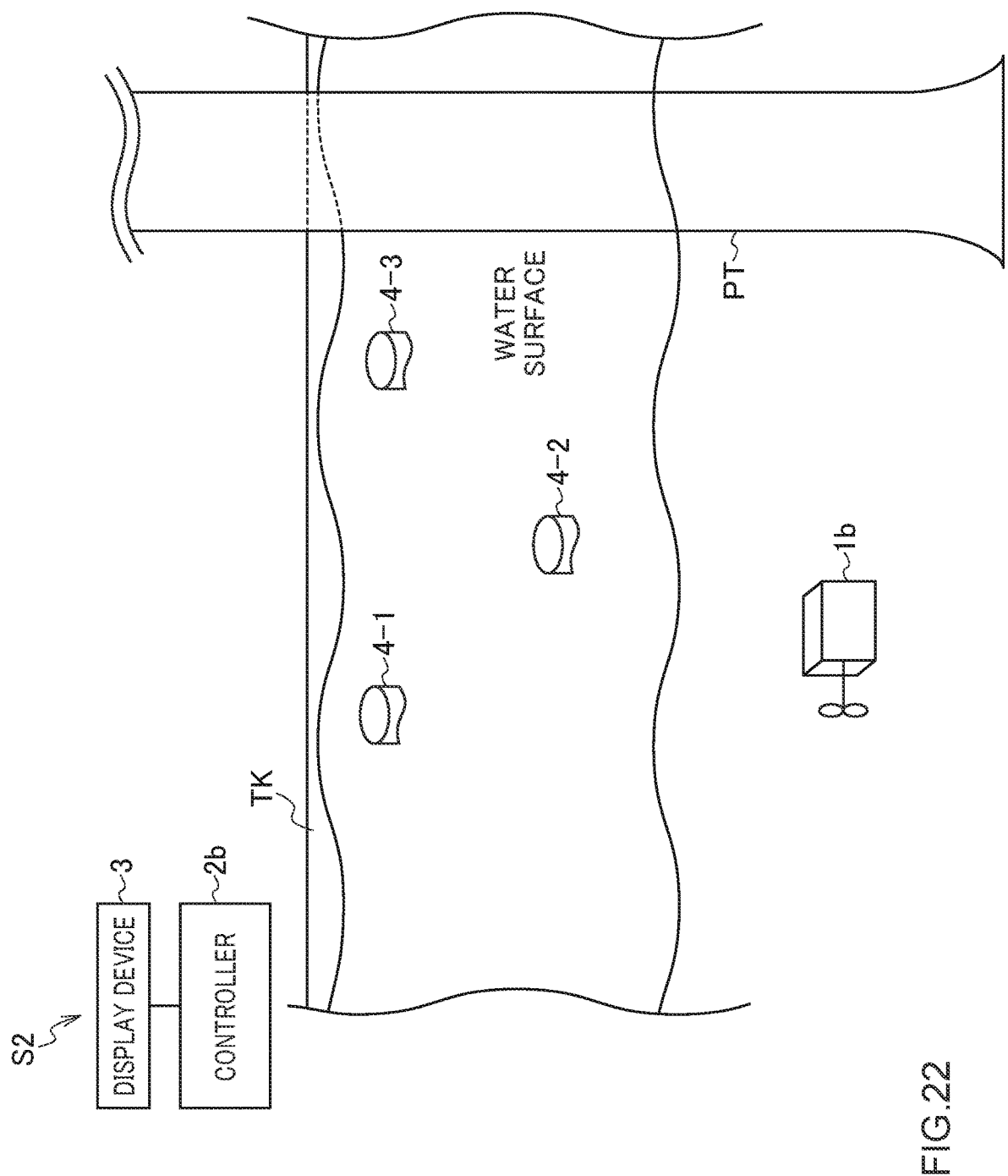
FIG. 22 is a block diagram illustrating a schematic configuration of an underwater robot control system according to a second embodiment.

Next, a second embodiment will be described. FIG. 22 is a block diagram illustrating a schematic configuration of an underwater robot control system according to the second embodiment. As illustrated in FIG. 22, an underwater robot control system S2 according to the second embodiment includes an underwater robot 1b movable in water, three communication buoys 4-1, 4-2, and 4-3 floating on a water surface, a controller 2b, and a display device 3.

Figure 23:
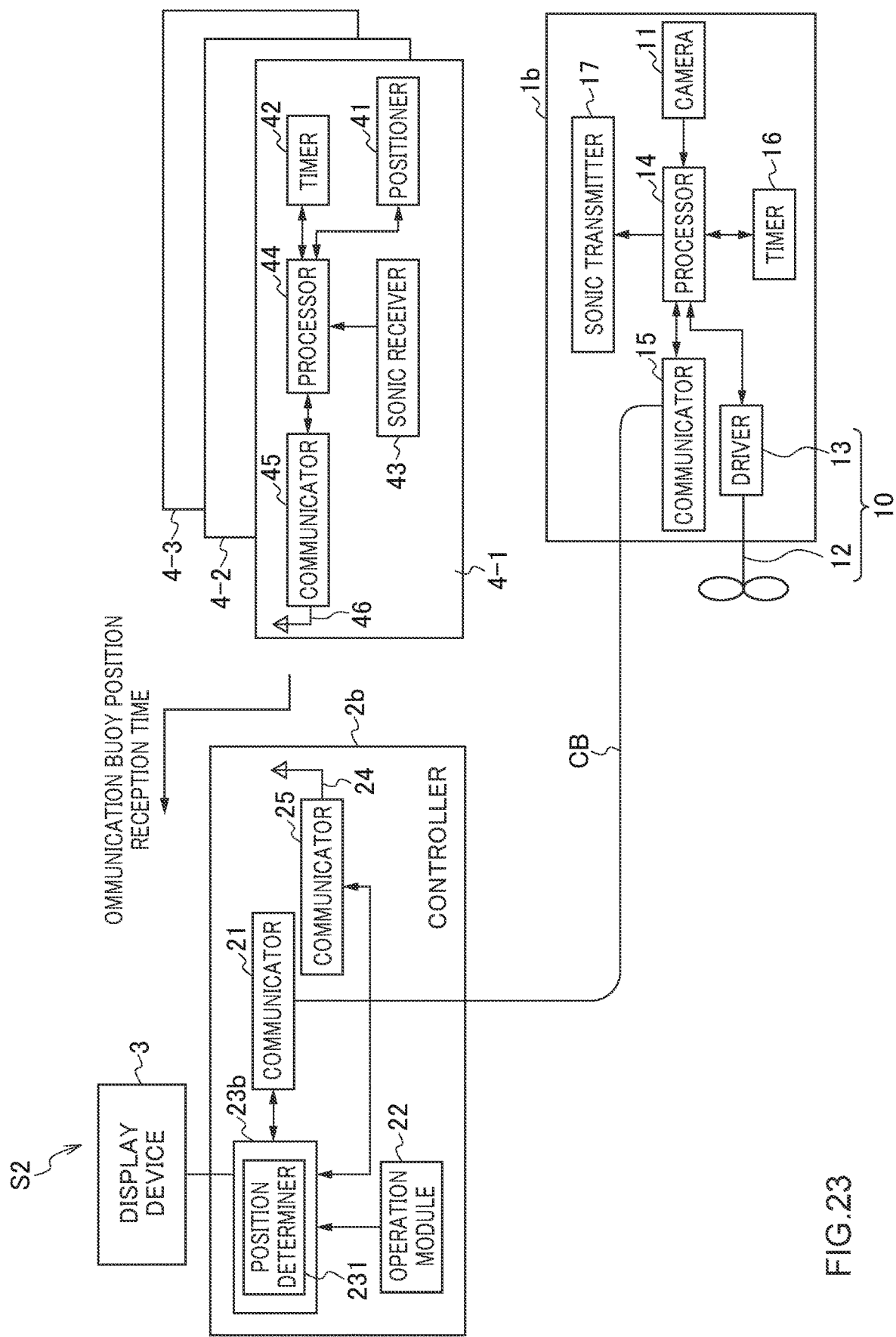
FIG. 23 is a block diagram illustrating a schematic configuration of the underwater robot control system according to the second embodiment.

FIG. 23 is a block diagram illustrating a schematic configuration of the underwater robot control system S2 according to the second embodiment. The underwater robot control system S2 according to the second embodiment in FIG. 23 differs from the underwater robot control system S1 of the first embodiment in FIG. 20 in that the underwater robot 1 is changed to the underwater robot 1b and the controller 2 is changed to the controller 2b.

The underwater robot 1b according to the present embodiment is capable of transmitting a sonic wave. The underwater robot 1b according to the present embodiment has a configuration in which a timer 16 and a sonic transmitter 17 are added, as compared with the underwater robot 1 according to the first embodiment. The timer 16 and the sonic transmitter 17 are connected to a processor 14 via a bus. The underwater robot 1b is capable of performing imaging in water.

The timer 16 counts time. The time in the timer 16 is synchronized with the time in the communication buoys 4-1, 4-2, and 4-3 in advance.

The sonic transmitter 17 transmits a sonic wave (Ping wave). For example, the sonic transmitter 17 transmits a sonic wave at a predetermined time.

Since the communication buoys 4-1, 4-2, and 4-3 have the same configuration, the configuration of the communication buoy 4-1 will be described as a representative.

The communication buoy 4-1 includes a positioner 41, a timer 42, a sonic receiver 43, a processor 44, a communicator 45, and an antenna 46. The processor 44 is connected to other elements via a bus.

The positioner 41 is an example of a position detector that detects respective positions of the communication buoys 4-1, 4-2, and 4-3. The positioner 41 is, for example, a global positioning system (GPS) receiver, and provided in the communication buoy 4-1 and which measures the position of the communication buoy 4-1.

The timer 42 counts time. As described above, the time in the timer 42 is synchronized with the time in the timer 16 of the underwater robot 1b in advance.

The sonic receiver 43 receives the sonic wave transmitted from the sonic transmitter 17 of the underwater robot 1b. When the sonic receiver 43 has received the sonic wave, the processor 44 acquires the time at which the sonic receiver 43 has received the sonic wave (hereinafter the time is referred to as reception time) from the timer 42.

The communicator 45 can wirelessly communicate with the controller 2b via the antenna 46. The processor 44 causes the communicator 45 to transmit the acquired reception time and the position of the communication buoy 4-1 to the controller 2b.

The controller 2b according to the second embodiment is different from the controller 2 according to the first embodiment in that the processor 23 is changed to a processor 23b, and an antenna 24 and a communicator 25 are added.

The communicator 25 wirelessly receives the reception times transmitted by the communication buoys 4-1 to 4-3 and the positions of the communication buoys 4-1 to 4-3 via the antenna 24.

The processor 23b functions as a position determiner 231 by reading and executing a program. The position determiner 231 determines the position of the underwater robot 1, using differences between a transmission time of the sonic wave and the reception times when the communication buoys 4-1 to 4-3 have received the sonic wave, and the respective positions of the communication buoys 4-1 to 4-3. To be specific, the position determiner 231 determines a distance between each of the communication buoys 4-1 to 4-3 and the underwater robot 1, using the differences between the transmission time of the sonic wave and the reception times when the respective communication buoys 4-1 to 4-3 have received the sonic wave, and determines the position of the underwater robot 1 on the basis of the determined distances and the respective positions of the communication buoys 4-1 to 4-3.

Further, the position determiner 231 moves the underwater robot 1 by a predetermined distance and stops the underwater robot 1, and after the stop, the position determiner 231 determines the position of the underwater robot 1 after stop, using the differences between the transmission time of the sonic wave and the reception times when the communication buoys 4-1 to 4-3 have received the sonic wave, and the respective positions of the communication buoys 4-1 to 4-3. The position determiner 231 determines the direction of the underwater robot 1, using positions of the underwater robot 1 before and after movement. The position determiner changes the direction of the underwater robot 1 toward an inspection target (here, a pumping pipe of a pump, for example), using the direction of the underwater robot 1. Here, the inspection target is an object to be inspected, explored, or targeted.

Figure 24:
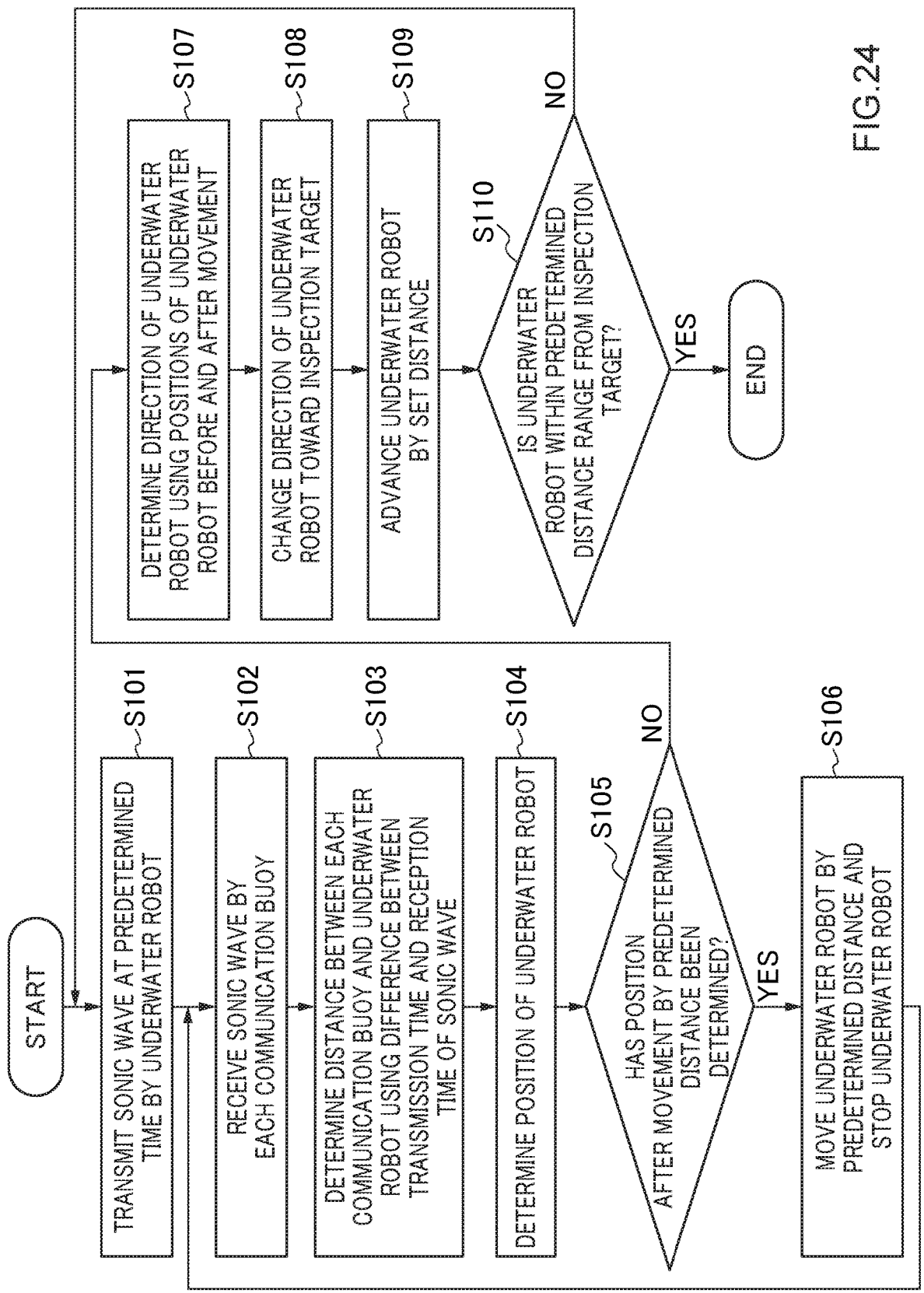
FIG. 24 is a flowchart illustrating an example of a flow of the underwater robot control method according to the second embodiment.

FIG. 24 is a flowchart illustrating an example of a flow of the underwater robot control method according to the second embodiment.

(Step S101) First, the underwater robot transmits a sonic wave at a predetermined time.

(Step S102) Next, each of the communication buoys 4-1 to 4-3 receives the sonic wave.

(Step S103) Next, the position determiner 231 determines the distances between the communication buoys 4-1 to 4-3 and the underwater robot 1, using the differences between the transmission time of the sonic wave and the respective reception times of the communication buoys 4-1 to 4-3.

(Step S104) Next, the position determiner 231 determines the position of the underwater robot 1 on a three-dimensional space on the basis of the distances determined in step S103 and the respective positions of the communication buoys 4-1 to 4-3. Here, the number of intersections of three spheres respectively having the three distances determined in step S103 as radiuses is two but one of the two intersections is in the air, and thus the other intersection existing in water is the position of the underwater robot 1 in the three-dimensional space.

(Step S105) Next, the position determiner 231 determines whether the position of the underwater robot 1 has been determined after advancing the underwater robot 1 by a predetermined distance. When the position of the underwater robot 1 after advancing the underwater robot 1 by the predetermined distance is determined, the processing proceeds to step S107.

(Step S106) When the position of the underwater robot 1 after advancing the underwater robot 1 by the predetermined distance is not determined in step S105, the position determiner 231 moves the underwater robot by a predetermined distance (for example, 1 m) (for example, advancing or retracting the underwater robot 1) while maintaining the depth, and stops the underwater robot 1. Then, returning to step S102, the processing of steps S102 to S104 is executed after the movement, and the position of the underwater robot after the movement is determined.

(Step S107) When the position of the underwater robot 1 after advancing the underwater robot 1 by the predetermined distance is determined in step S105, the position determiner 231 determines the direction of the underwater robot 1, using the positions of the underwater robot 1 before and after the movement (for example, advancing or retracting).

(Step S108) Next, the position determiner 231 changes the direction of the underwater robot 1 toward the inspection target, using the direction of the underwater robot 1 determined in step S107.

(Step S109) Next, the processor 23b advances the underwater robot 1 by a set distance.

(Step S110) Next, the processor 23b determines whether the underwater robot 1 is within a predetermined distance range from the inspection target. When the underwater robot 1 is not within the predetermined distance range from the inspection target (here, the pumping pipe of the pump as an example), the processing returns to step S101 and is repeated. When the underwater robot 1 is within the predetermined distance range from the inspection target, the processing of the present flowchart is terminated.

As described above, the underwater robot control system S2 of a remote control type according to the second embodiment includes the underwater robot 1 capable of transmitting the sonic wave and including propulsion mechanism. Further, the underwater robot control system S2 includes the three communication buoys 4-1 to 4-3 capable of receiving the sonic wave transmitted by the underwater robot 1, capable of transmitting the reception time when the sonic wave is received, and floating on the water surface. Further, the underwater robot control system S2 includes the positioner 41 as a position detector for detecting the respective positions of the communication buoys 4-1 to 4-3. Further, the underwater robot control system S2 includes the communicator 25 that receives the reception times transmitted by the communication buoys 4-1 to 4-3. Further, the underwater robot control system S2 includes the position determiner 231 that determines the position of the underwater robot 1, using the differences between the transmission time of the sonic wave and the reception times when the communication buoys 4-1 to 4-3 have received the sonic wave, and the respective positions of the communication buoys.

With the configuration, the operator can grasp the position of the underwater robot 1 even in the case where the underwater robot 1 in water cannot be seen from the operator, and thus the remote control can be facilitated.

Note that, in the second embodiment, the description has been given such that the number of communication buoys is three. However, the number of communication buoys is not limited to three, and four or more communication buoys may be used.

Further, in the second embodiment, the positioner 41 as an example of the position detector has measured the position of its own communication buoy. However, the position detector is not limited thereto, and the position detector may image the communication buoys 4-1 to 4-3, perform image processing for image data obtained through the imaging, and specify the positions of the communication buoys 4-1 to 4-3.

Further, the communicator 25 and the communicator 45 have communicated by wireless means. However, wired means may be used.

Third Embodiment

Next, a third embodiment will be described. In the third embodiment, a position of an underwater robot 1 is measured by a sonar provided in each communication buoy, unlike the second embodiment. With the configuration, the position of the underwater robot 1 can be measured in nearly real time.

Figure 25:
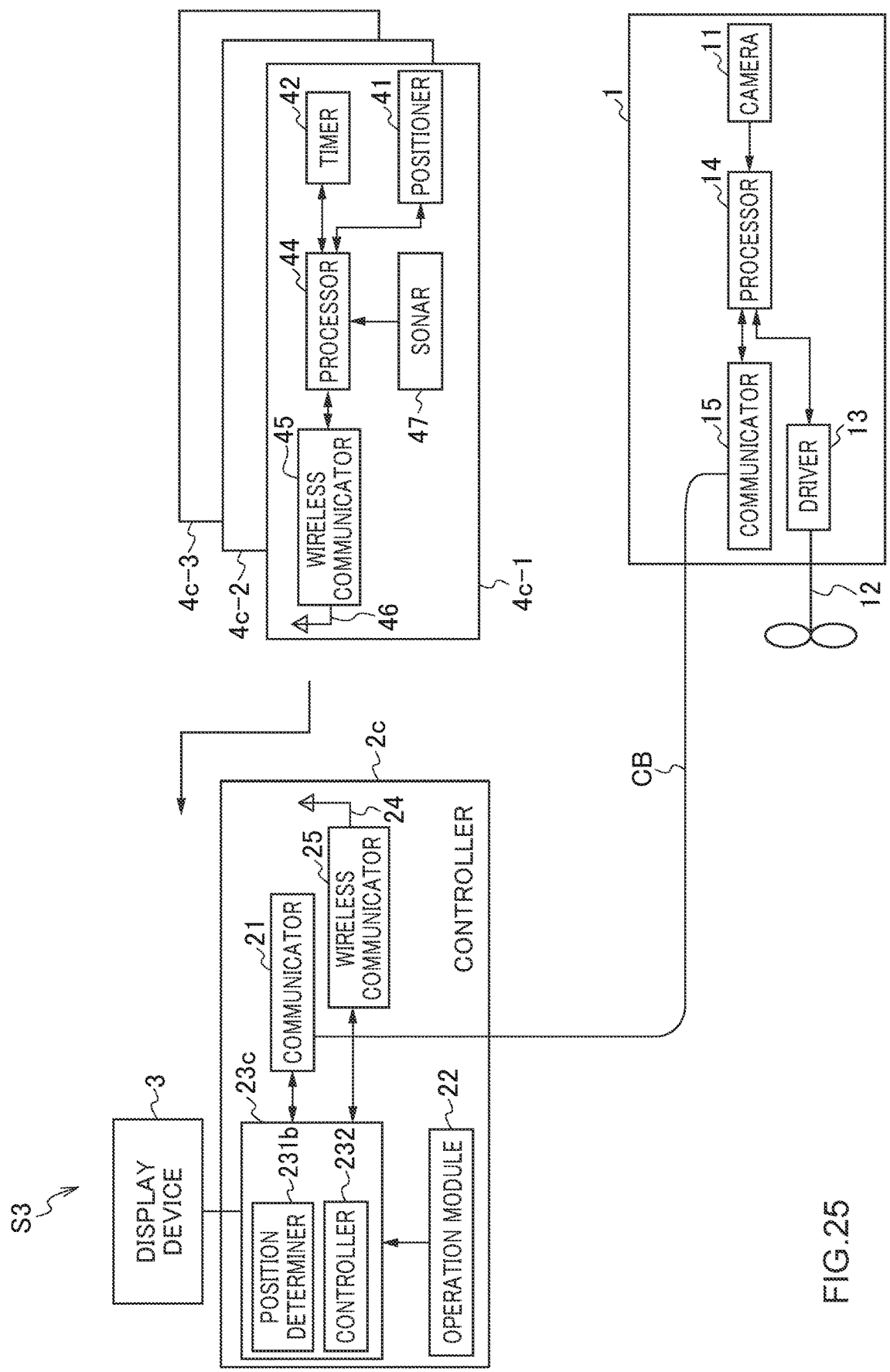
FIG. 25 is a block diagram illustrating a schematic configuration of an underwater robot control system according to a third embodiment.

FIG. 25 is a block diagram illustrating a schematic configuration of an underwater robot control system according to the third embodiment. As illustrated in FIG. 25, an underwater robot control system S3 according to the third embodiment includes an underwater robot 1, three communication buoys 4c-1, 4c-2, and 4c-3 floating on a water surface, a controller 2c, and a display device 3.

The underwater robot 1 is capable of imaging an object placed in water and including a propulsion mechanism. Since the underwater robot 1 according to the present embodiment has the same configuration as the underwater robot 1 according to the first embodiment, detailed description will be omitted. Since the communication buoys 4c-1, 4c-2, and 4c-3 have the same configuration, the configuration of the communication buoy 4c-1 will be described as a representative.

The communication buoy 4c-1 has a configuration in which the sonic receiver 43 is deleted and a sonar 47 is added, as compared with the communication buoy 4-1 according to the second embodiment in FIG. 23. The sonar 47 is capable of transmitting an ultrasonic wave and is capable of capturing a reflection wave of the ultrasonic wave. As an example of a position detector, a positioner 41 that detects the position of its own communication buoy is included.

The controller 2c according to the present embodiment is different from the controller 2b according to the second embodiment in that the processor 23b is changed to a processor 23c. The processor 23c functions as a position determiner 231b and a control module 232 by reading and executing a program.

The position determiner 231b determines the position of the underwater robot 1, using an observation result by the sonar 47 included in the communication buoy 4c-1 and the position of the communication buoy 4c-1. Specifically, for example, the position determiner 231b may determine a direction in which the ultrasonic wave is returned as the direction of the underwater robot 1, using a time required from when the ultrasonic wave is transmitted to when the ultrasonic wave is reflected at the underwater robot 1 and is returned, and may determine the position of the underwater robot 1, using the distance, the direction, and the position of the communication buoy.

Note that the position determiner 231b may determine the position of the underwater robot 1, using the observation result by the sonar 47 included in the communication buoy 4c-2 and the position of the communication buoy 4c-2. Further, the position determiner 231b may determine the position of the underwater robot 1, using the observation result by the sonar 47 included in the communication buoy 4c-3 and the position of the communication buoy 4c-3.

The control module 232 feedback controls and/or feedforward controls the underwater robot 1 to make a difference between the position of the underwater robot 1 and a position on a locus from the underwater robot 1 to the inspection target (here, a pump, as an example) minimum. The position on a locus may be, for example, a position separated from the current position of the underwater robot 1 by a set distance on the locus. With the control, the controller 232 can guide the underwater robot 1 to a destination by continuing the control.

Figure 26:
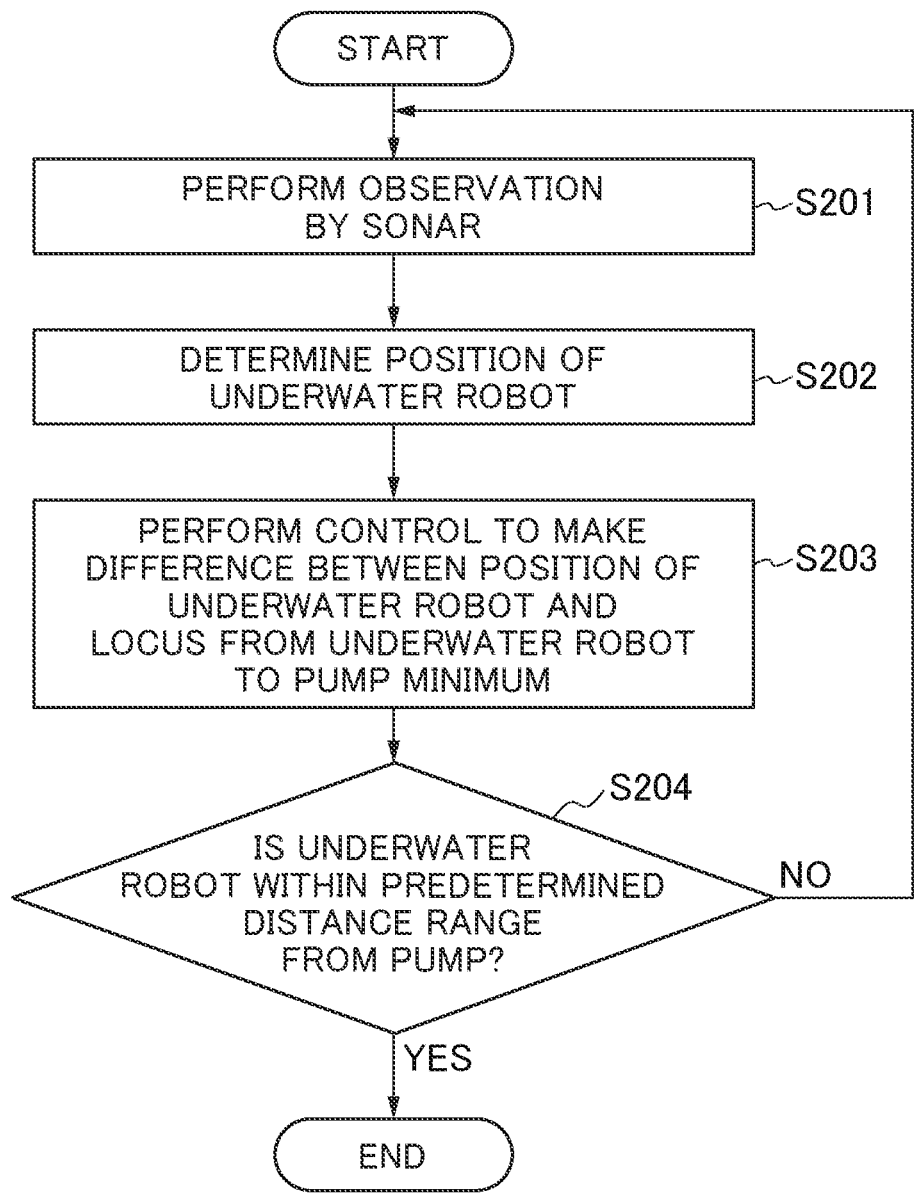
FIG. 26 is a flowchart illustrating an example of a flow of an underwater robot control method according to the third embodiment.

FIG. 26 is a flowchart illustrating an example of a flow of an underwater robot control method according to the third embodiment.

(Step S201) First, the communication buoy 4c-1 observes the underwater robot 1 by the sonar 47.

(Step S202) Next, the position determiner 231b determines the position of the underwater robot 1, using the observation result by the sonar 47 included in the communication buoy 4c-1 and the position of the communication buoy 4c-1.

(Step S203) Next, the control module 232 controls the underwater robot 1 to make the difference between the position of the underwater robot 1 and the position on the locus from the underwater robot 1 to the pump as the inspection target minimum.

(Step S204) Next, the control module 232 determines whether the underwater robot 1 is within a predetermined distance range from the pump as the inspection target. When the underwater robot 1 is not within the predetermined distance range from the pump as the inspection target, the processing returns to step S201 and is continued. When the underwater robot 1 is within the predetermined distance range from the pump as the inspection target, the processing in the control module 232 is terminated.

The underwater robot control system S3 of a remote control type according to the third embodiment includes the underwater robot 1 capable of imaging the inspection target placed in water and including the propulsion mechanism, the communication buoys 4c-1 to 4c-3 including a sonar capable of transmitting an ultrasonic wave and capable of capturing a reflection wave of the ultrasonic wave, and floating on the water surface, the positioner 41 as the position detector configured to detect the positions of the communication buoys 4c-1 to 4c-3, and the position determiner configured to determine the position of the underwater robot 1, using the observation result by the sonar 47 and the positions of the communication buoys 4c-1 to 4c-3.

With the configuration, the operator can grasp the position of the underwater robot 1 even in the case where the underwater robot 1 in water cannot be seen from the operator, and thus the remote control can be facilitated.

Note that, in the third embodiment, the description has been given such that the number of communication buoys is three. However, the number of communication buoys is not limited to three, and one, two, or four or more communication buoys may be used.

Fourth Embodiment

Next, a fourth embodiment will be described. In the fourth embodiment, a communication buoy includes a synthetic aperture sonar capable of transmitting a sonic wave to a plurality of directions. The synthetic aperture sonar acquires a sonar image including an underwater robot 1 and a pumping pipe PT of a pump as an inspection target. This sonar image is updated and displayed on a display device 3. With the display, an operator can guide and bring the underwater robot 1 close to the pumping pipe PT of the pump as the inspection target while watching the image.

Figure 27:
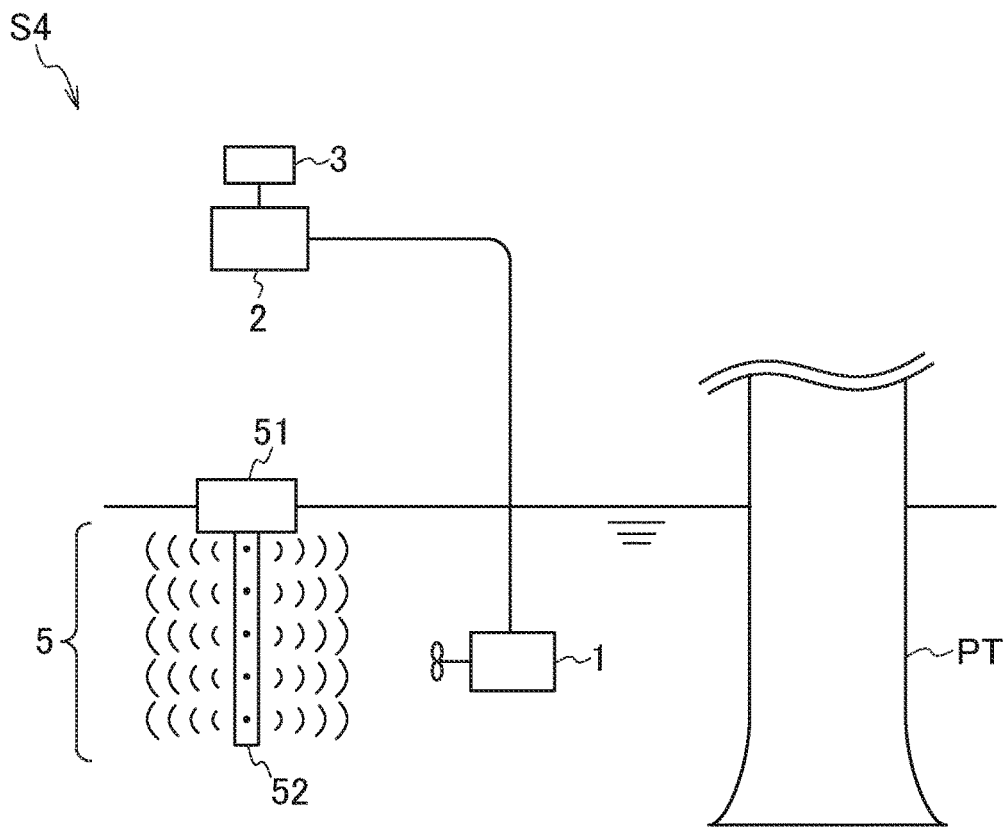
FIG. 27 is a block diagram illustrating a schematic configuration of an underwater robot control system according to a fourth embodiment.

FIG. 27 is a block diagram illustrating a schematic configuration of an underwater robot control system according to the fourth embodiment. As illustrated in FIG. 27, an underwater robot control system S4 includes an underwater robot 1, a controller 2 for operating the underwater robot 1 from a remote place (for example, on water, on land, etc.), a display device 3, and a communication buoy 5. The display device 3 displays a picture or a sonar image imaged by the underwater robot 1. Since the underwater robot 1, the controller 2, and the display device 3 according to the present embodiment have the same configurations as those according to the first embodiment, detailed description will be omitted.

The communication buoy 5 includes a floating member 51 capable of floating on water, and a synthetic aperture sonar 52 capable of transmitting a sonic wave toward a plurality of directions. In the present embodiment, as an example, the synthetic aperture sonar 52 can acquire omnidirectional sonar images. With the configuration, sonar images in a plurality of directions can be acquired at a time, and therefore the possibility of acquiring a sonar image of the underwater robot 1 can be improved regardless of the direction of the underwater robot 1 in water. Here, the synthetic aperture sonar 52 is an example of a sonic transmitter connected to the floating member 51 so that the synthetic aperture sonar 52 can be arranged in water and capable of transmitting a sonic wave and receiving a reflected sonic wave from the underwater robot 1.

Figure 28:
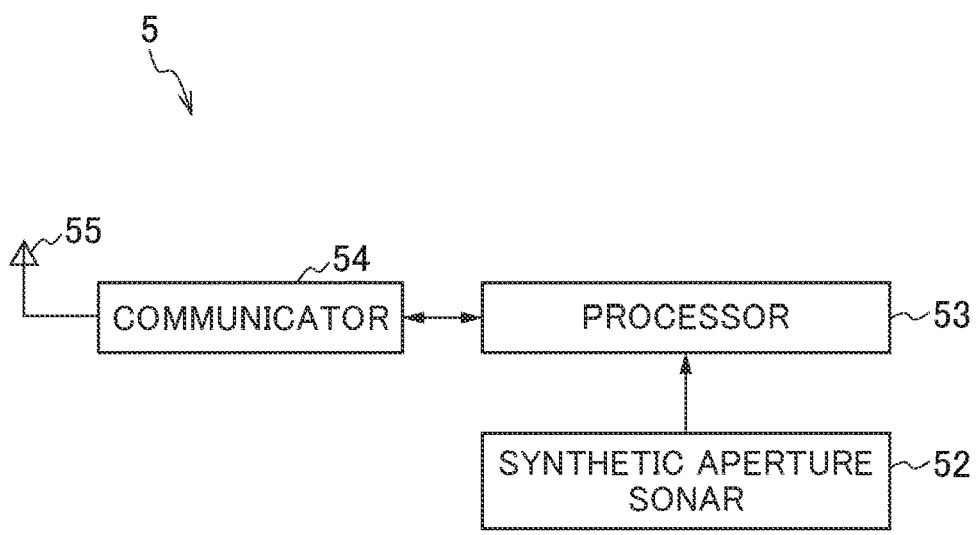
FIG. 28 is a block diagram illustrating a schematic functional configuration of a communication buoy according to the fourth embodiment.

FIG. 28 is a block diagram illustrating a schematic functional configuration of a communication buoy according to the fourth embodiment. As illustrated in FIG. 28, the communication buoy 5 further includes a processor 53, a communicator 54, and an antenna 55. The processor 53 generates image data of the sonar image, using the sonic wave received by the synthetic aperture sonar 52, by reading and executing a program. The communicator 54 transmits an image signal including the generated image data to the controller 2 via the antenna 55. As a result, the controller 2 receives the image signal and displays the sonar image on the display device 3. The sonar image displayed on the display device 3 is updated as needed, as the series of processing is repeated at fixed intervals, for example.

Figure 29:
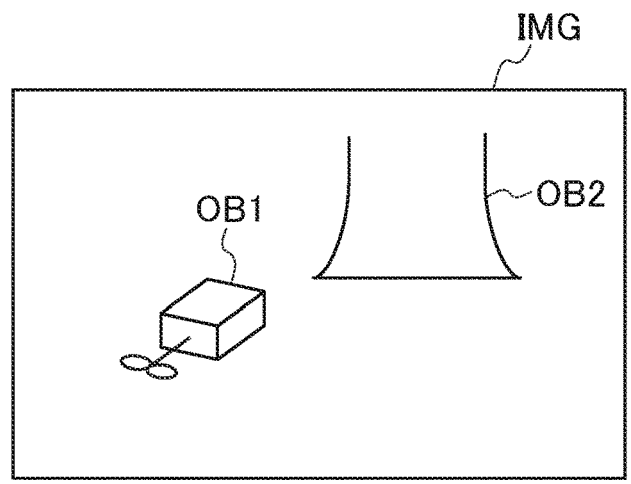
FIG. 29 is a schematic diagram illustrating an example of a sonar image.

FIG. 29 is a schematic diagram illustrating an example of the sonar image. As illustrated in FIG. 29, a sonar image IMG includes an object OB1 representing the underwater robot 1 and an object OB2 representing the pumping pipe PT of the pump. With the configuration, an operator can guide and bring the underwater robot 1 close to the pumping pipe PT of the pump while watching the sonar image IMG.

As described above, the underwater robot control system S4 of a remote control type according to the fourth embodiment includes the underwater robot 1 capable of imaging the inspection target arranged in water and including the propulsion mechanism, and the communication buoy 5 floating on water. The communication buoy 5 includes the floating member 51 floating on water, the synthetic aperture sonar 52 as an example of a sonic transmitter connected to the floating member 51 so that the synthetic aperture sonar 52 can be arranged in water, and capable of transmitting a sonic wave and receiving a sonic wave reflected from the underwater robot 1, the processor 53 that generates the image data, using the sonic wave received by the synthetic aperture sonar 52, and the communicator 54 that transmits the image signal including the generated image data.

With the configuration, the operator can grasp a positional relationship between the underwater robot 1 and the inspection target from the image data even in the case where the underwater robot 1 in water cannot be seen from the operator, and thus the remote control can be facilitated.

Note that the controller 2 may create a three-dimensional diagram of a structure in water on the basis of a generated sonar image. Further, in a case where there is a three-dimensional CAD diagram of a structure in the water in advance, the controller 2 may modify the three-dimensional diagram of the structure on the basis of the sonar image using the three-dimensional CAD diagram.

(First Modification of Fourth Embodiment)

Figure 30:
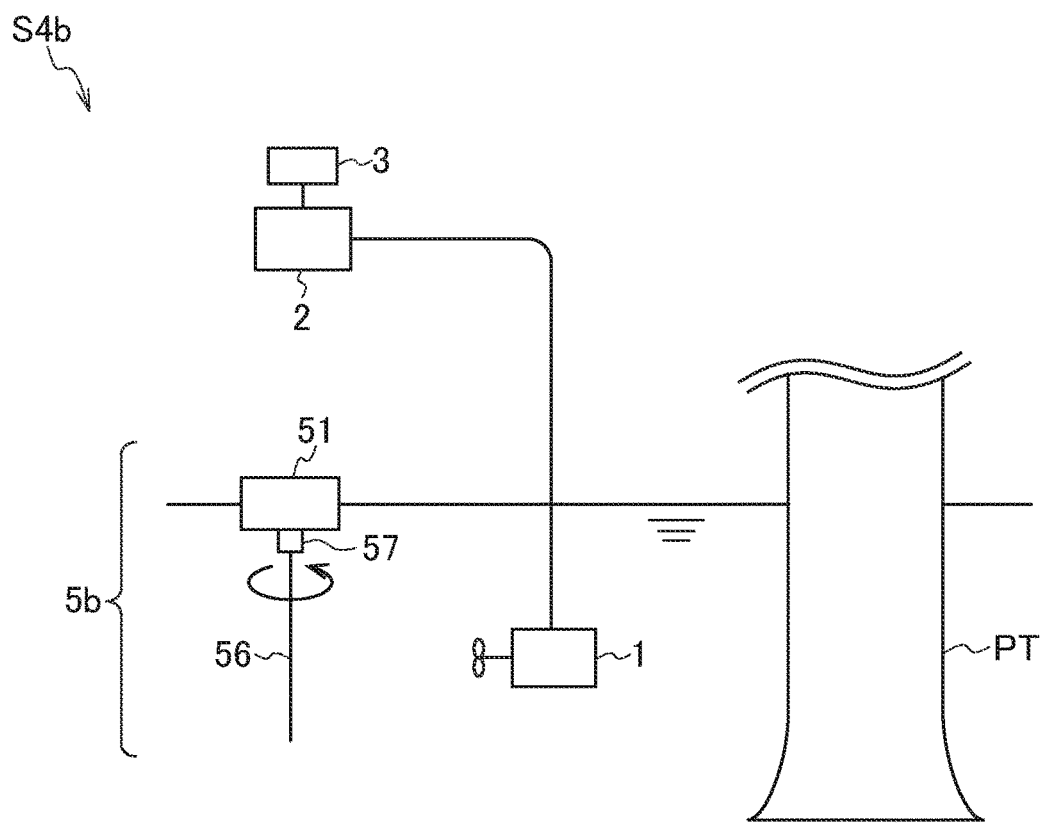
FIG. 30 is a block diagram illustrating a schematic configuration of an underwater robot control system according to a first modification of the fourth embodiment.

Next, a first modification of the fourth embodiment will be described. In the first modification, a synthetic aperture sonar capable of transmitting a sonic wave in one direction is rotated to perform scanning. FIG. 30 is a block diagram illustrating a schematic configuration of an underwater robot control system according to the first modification of the fourth embodiment. As illustrated in FIG. 30, an underwater robot control system S4b according to the first modification of the fourth embodiment is different from the underwater robot control system S4 in FIG. 27 in that the communication buoy 5 is changed to a communication buoy 5b. The communication buoy 5b has a configuration in which the synthetic aperture sonar 52 is changed to a synthetic aperture sonar 56 capable of transmitting a sonic wave in one direction, and a driver 57 that rotates the synthetic aperture sonar 56 is added, as compared with the communication buoy 5 in FIG. 27. The synthetic aperture sonar 56 is connected to a floating member 51 via the driver 57 so as to be arrangeable in water.

With the configuration, the synthetic aperture sonar 56 can be rotated to perform scanning, and sonar images in a plurality of direction can be acquired. Therefore, a sonar image of the underwater robot can be acquired regardless of the direction of the underwater robot. Here, the synthetic aperture sonar 56 is an example of a sonic transmitter capable of transmitting a sonic wave and receiving a sonic wave reflected from the underwater robot 1.

(Second Modification of Fourth Embodiment)

Figure 31:
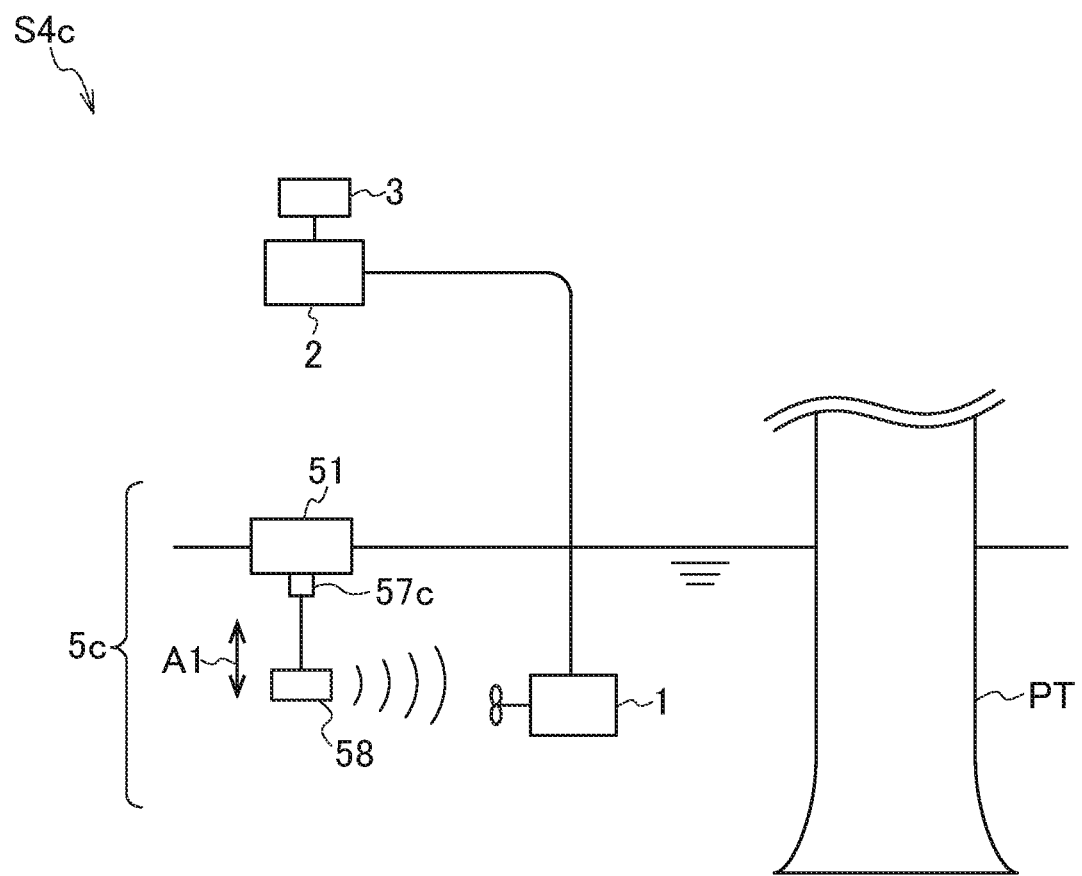
FIG. 31 is a block diagram illustrating a schematic configuration of an underwater robot control system according to a second modification of the fourth embodiment.

Next, a second modification of the fourth embodiment will be described. In the second modification, a transducer is moved up and down for scanning. FIG. 31 is a block diagram illustrating a schematic configuration of an underwater robot control system according to the second modification of the fourth embodiment. As illustrated in FIG. 31, an underwater robot control system S4c according to the second modification of the fourth embodiment is different from the underwater robot control system S4 in FIG. 27 in that the communication buoy 5 is changed to a communication buoy 5c. The communication buoy 5c has a configuration in which the synthetic aperture sonar 52 is changed to a transducer 58, and a driver 57c that moves the transducer 58 up and down is added, as compared with the communication buoy 5 in FIG. 27. The transducer 58 is connected to a floating member 51 via the driver 57c so as to be arrangeable in water.

With the configuration, the transducer 58 can be moved up and down to perform scanning, and a sonar image in a depth direction can be acquired. Therefore, a sonar image of the underwater robot 1 can be acquired regardless of the depth in water of the underwater robot 1. Here, the transducer 58 is an example of a sonic transmitter capable of transmitting a sonic wave and receiving a sonic wave reflected from the underwater robot 1.

(Third Modification of Fourth Embodiment)

Figure 32:
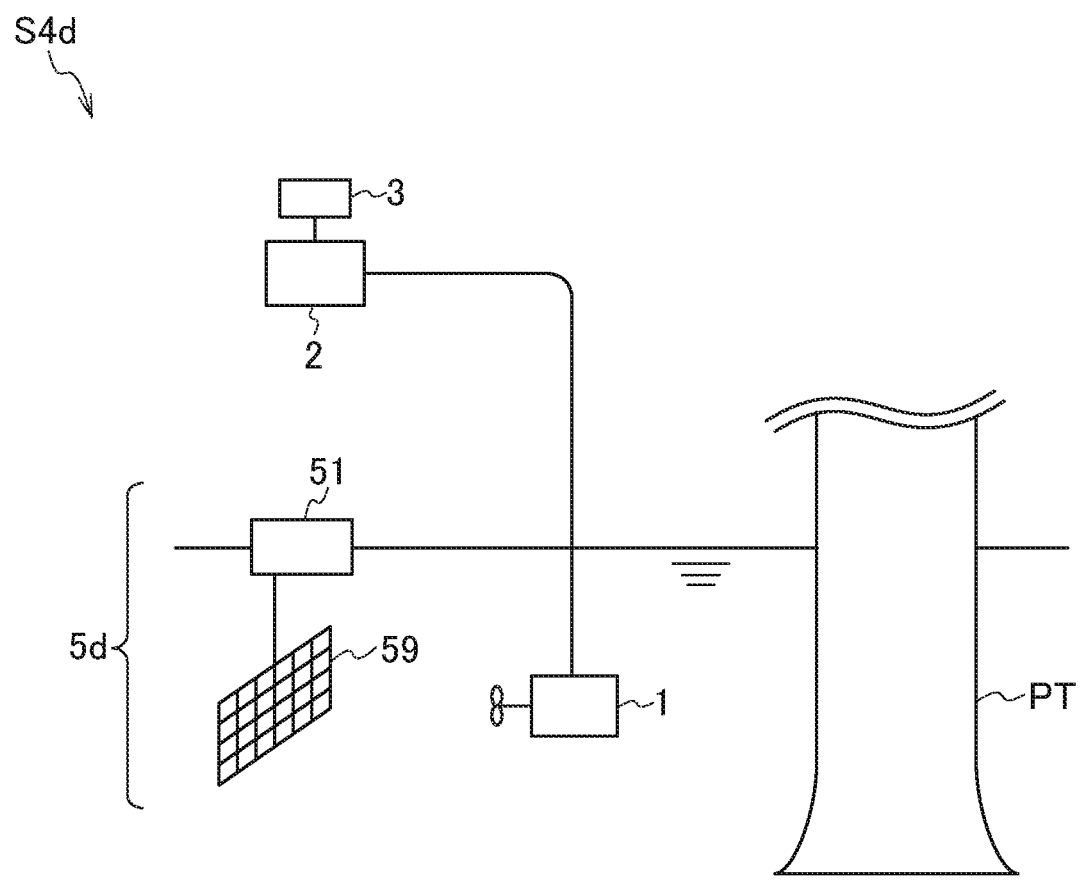
FIG. 32 is a block diagram illustrating a schematic configuration of an underwater robot control system according to a third modification of the fourth embodiment.

Next, a third modification of the fourth embodiment will be described. In the third modification, scanning is performed with a transducer array in which a plurality of transducers is arranged in an approximately planar manner. FIG. 32 is a block diagram illustrating a schematic configuration of an underwater robot control system according to the third modification of the fourth embodiment. As illustrated in FIG. 32, an underwater robot control system S4d according to the third modification of the fourth embodiment is different from the underwater robot control system S4 in FIG. 27 in that the communication buoy 5 is changed to a communication buoy 5d. The communication buoy 5d has a configuration in which the synthetic aperture sonar 52 is changed to a transducer array 59, as compared with the communication buoy 5 in FIG. 27. The transducer array 59 is obtained by arranging a plurality of transducers in substantially the same plane and is connected to a floating member 51 so as to be arrangeable in water.

With the configuration, the transducer array 59 can be used to perform scanning, and a sonar image in a predetermined range in the depth direction can be acquired at a time. Therefore, a sonar image including the underwater robot 1 can be easily acquired. Here, the transducer array 59 is an example of a sonic transmitter capable of transmitting a sonic wave and receiving a sonic wave reflected from the underwater robot 1.

Fifth Embodiment

Next, a fifth embodiment will be described. In an underwater robot control system according to the fifth embodiment, an underwater robot itself includes an acoustic camera that captures an underwater picture by an ultrasonic wave to generate image data, and an operator brings the underwater robot close to an inspection target while watching the image data.

Figure 33:
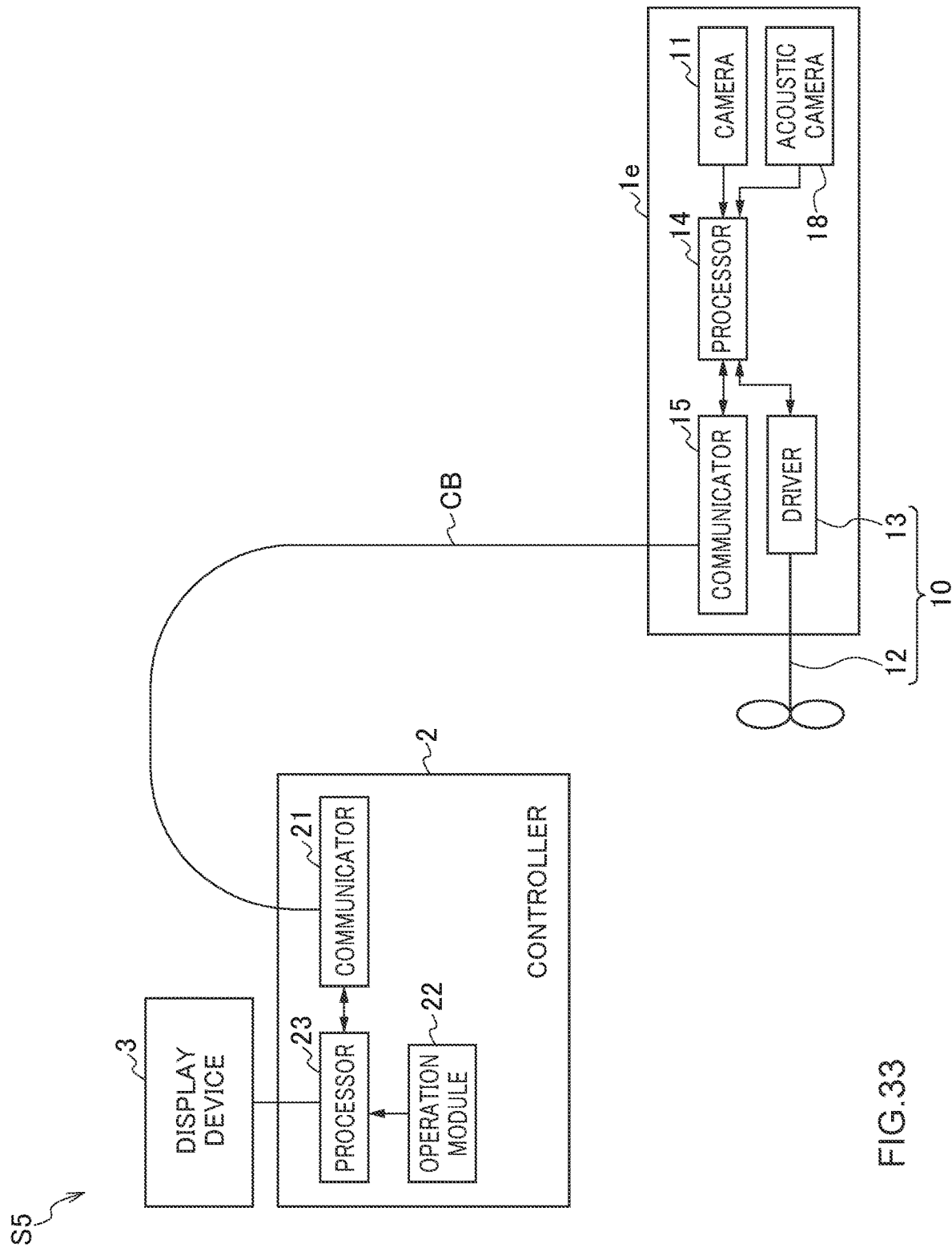
FIG. 33 is a block diagram illustrating a schematic configuration of an underwater robot control system according to a fifth embodiment.

FIG. 33 is a block diagram illustrating a schematic configuration of an underwater robot control system according to the fifth embodiment. As illustrated in FIG. 33, an underwater robot control system S5 according to the fifth embodiment differs from the underwater robot control system S1 of the first embodiment in that the underwater robot 1 is changed to an underwater robot 1e.

The underwater robot 1e has a configuration in which an acoustic camera 18 is added, as compared with the underwater robot 1 in FIG. 20, and the acoustic camera 18 captures an underwater picture by an ultrasonic wave to generate image data. A processor 14 causes a communicator 15 to transmit an image signal including the image data to a controller 2 via a cable CB. As a result, a communicator 21 of the controller 2 receives the image signal, and a processor 23 of the controller 2 displays the image data on a display device 3. The image data is updated and displayed as the series of processing is performed at predetermined intervals, for example.

Figure 34:
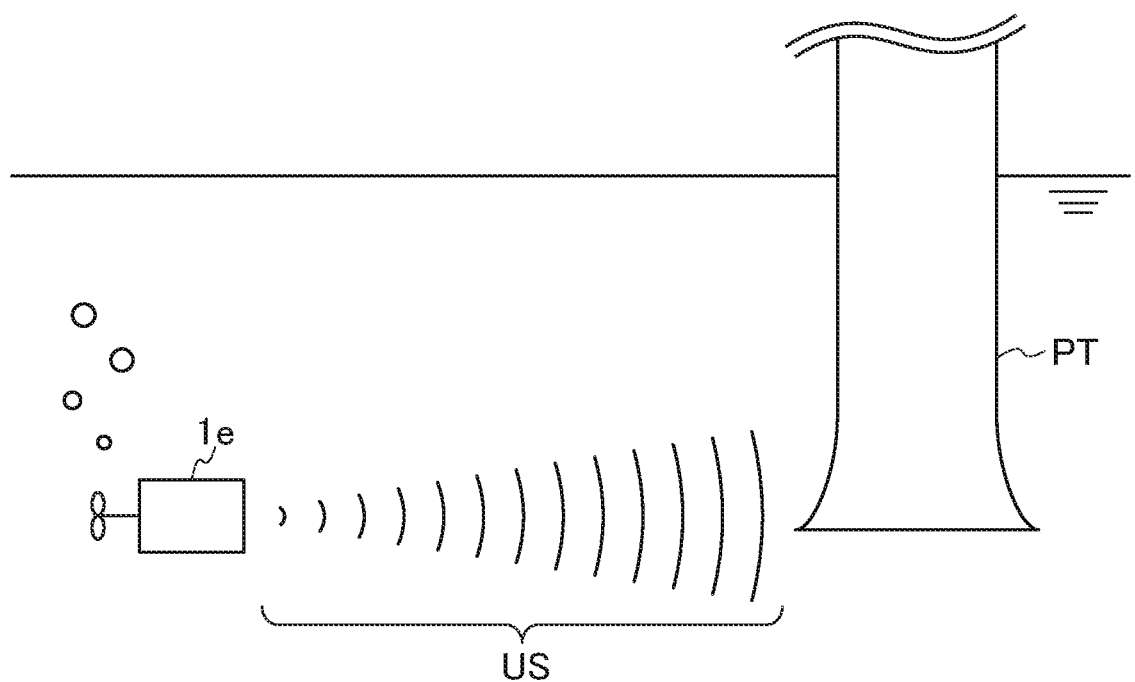
FIG. 34 is a schematic diagram for describing an underwater robot control method according to the fifth embodiment.

FIG. 34 is a block diagram illustrating a schematic configuration of the underwater robot control system according to the fifth embodiment. FIG. 34 illustrates the underwater robot 1e that transmits an ultrasonic wave US in muddy water. As illustrated in FIG. 34, an operator can bring the underwater robot 1 close to a pumping pipe PT of the pump as an inspection target while watching the image data that is updated and displayed on the display device 3 as needed.

The underwater robot control system S5 of a remote control type according to the fifth embodiment includes the underwater robot 1e including the acoustic camera 18 that captures an underwater picture by an ultrasonic wave to generate image data, and the communicator 15 that transmits the image data, and including a propulsion mechanism 10, the display device 3, and the controller 2 that receives the image data and displays the image data on the display device 3. The controller 2 controls the underwater robot 1e to move the underwater robot 1e according to an operation by the operator.

With the configuration, the operator can bring the underwater robot 1 close to the inspection target (here, the pumping pipe PT of a pump, as an example) while watching the image data that is updated and displayed on the display device 3, as needed.

Further, in an underwater robot control method of a remote control type according to the fifth embodiment, the underwater robot 1e captures an underwater picture by an ultrasonic wave to generate image data, and the underwater robot 1e transmits the image data. Thereafter, the controller 2 receives the image data, the controller 2 displays the image data on the display device, and the controller 2 controls the underwater robot to move the underwater robot according to an operation by the operator.

With the configuration, the operator can bring the underwater robot 1 close to the inspection target (here, the pumping pipe PT of a pump, as an example) while watching the image data that is updated and displayed on the display device 3, as needed.

Note that the underwater robot 1e according to the present embodiment may further include a sonar.

Each of the first to fourth aspects described above is not limited to the above embodiment per se, and the constituent elements can be modified and embodied in the implementation stage without departing from the gist of the aspect. Further, various inventions can be formed by appropriately combining a plurality of the constituent elements disclosed in the above embodiments. For example, some constituent elements may be deleted from all the constituent elements illustrated in the embodiment.

Further, the constituent elements of different embodiments may be appropriately combined.

REFERENCE SIGNS LIST 1, 1b Underwater robot
10 Propulsion mechanism
11 Camera
12 Propeller
13 Driver
14 Processor
15 Communicator
16 Timer
17 Sonic transmitter 2 Controller
21 Communicator
22 Operation module
23 Processor
231, 231b Position determiner
232 Control module
23b, 23c Processor
24 Antenna
25 Communicator
2b, 2c Controller
3 Display device
4, 4c Communication buoy
41 Positioner
42 Timer
43 Sonic receiver
44 Processor
45 Communicator
46 Antenna
47 Sonar
5, 5b, 5c, 5d Communication buoy
51 Floating member
52, 56 Synthetic aperture sonar
53 Processor
54 Communicator
55 Antenna
57, 57c Driver
58 Transducer
59 Transducer array
S1, S2, S3, S4, S4b, S4c, S4d, S5 Underwater robot control system

The invention claimed is:

1. A pump inspection system comprising: an endoscope inserted into a pump; and an inspection device to which the endoscope is connected, wherein
the endoscope comprises:
a capture module including a plurality of cameras, and
a cable configured to transmit camera images obtained by the plurality of cameras to the inspection device, the plurality of cameras are arranged at different positions in the capture module to respectively obtain camera images of different capturing directions from one another, and
the inspection device comprises:
a storage in which, for each of a plurality of reference markers provided inside the pump, a position of the reference marker in the pump is stored,
a position determiner comprising a processor configured to determine a position of a distal end of the endoscope in the pump on the basis of camera images of an inside of the pump obtained by the plurality of cameras, and
a direction determiner comprising a processor configured to determine a direction into which the distal end of the endoscope faces in the pump on the basis of the camera images of an inside of the pump obtained by the plurality of cameras, calculates a distance from the distal end of the endoscope to the reference marker on the basis of two camera images that capture the same reference marker, among the camera images of an inside of the pump obtained by the plurality of cameras, and determines the position of the distal end of the endoscope in the pump on the basis of distances to at least three different reference markers and the positions of the reference markers in the pump.

2. The pump inspection system according to claim 1, wherein directional relationships between the capturing directions of the plurality of cameras and a direction of the distal end of the endoscope are stored in the storage, and
the direction determiner calculates the capturing direction of the camera that has captured the reference marker on the basis of an in-image position of the reference marker in the camera image that captures the reference marker, among the camera images of an inside of the pump obtained by the plurality of cameras, and obtains the direction into which the distal end of the endoscope faces on the basis of the directional relationship between the direction of the distal end of the endoscope and the capturing direction of the camera.

3. The pump inspection system according to claim 1, wherein the inspection device comprises a multi-display that respectively displays the camera images of an inside of the pump obtained by the plurality of cameras on a plurality of screens.

4. The pump inspection system according to claim 1, wherein
the inspection device comprises:
a spherical display processor that converts the camera images of an inside of the pump obtained by the plurality of cameras into spherical display images, and
a spherical display that displays the spherical display images on a spherical screen.

5. The pump inspection system according to claim 1, wherein
the inspection device comprises:
a stereoscopic display processor that converts the camera images of an inside of the pump obtained by the plurality of cameras into stereoscopic display images, and
a stereoscopic display that displays the stereoscopic display images on a stereoscopic display screen.

* * * * *